United States Patent
Lee et al.

(10) Patent No.: US 12,092,636 B2
(45) Date of Patent: Sep. 17, 2024

(54) SENSOR FOR LIQUID BIOPSY AND ITS METHOD OF MAKING, AND METHOD OF NON-INVASIVE LIQUID BIOPSY

(71) Applicant: City University of Hong Kong, Kowloon (HK)

(72) Inventors: Youngjin Lee, Seoul (KR); Abhimanyu Thakur, West Bengal (IN); Chi-Man Lawrence Wu, Kowloon (HK); Chen Xu, Nantong (CN); Siu-Pang Ng, Kowloon (HK)

(73) Assignee: City University of Hong Kong, Kowloon (HK)

( * ) Notice: Subject to any disclaimer, the term of this patent is extended or adjusted under 35 U.S.C. 154(b) by 368 days.

(21) Appl. No.: 16/839,158

(22) Filed: Apr. 3, 2020

(65) Prior Publication Data

US 2021/0311034 A1     Oct. 7, 2021

(51) Int. Cl.
| | |
|---|---|
| *G01N 33/543* | (2006.01) |
| *B01L 3/00* | (2006.01) |
| *C07K 16/22* | (2006.01) |
| *C07K 16/28* | (2006.01) |
| *G01N 33/574* | (2006.01) |

(52) U.S. Cl.
CPC ............ *G01N 33/543* (2013.01); *B01L 3/502* (2013.01); *C07K 16/22* (2013.01); *C07K 16/2884* (2013.01); *C07K 16/2896* (2013.01); *G01N 33/57488* (2013.01); *B01L 2300/0636* (2013.01); *B01L 2300/0803* (2013.01); *B01L 2300/0861* (2013.01); *B01L 2300/12* (2013.01); *B01L 2400/0484* (2013.01)

(58) Field of Classification Search
CPC ............ G01N 33/543; G01N 33/57488; B01L 3/502; B01L 2300/0636; B01L 2300/0803; B01L 2300/0861; B01L 2300/12; B01L 2400/0484; C07K 16/22; C07K 16/2884; C07K 16/2896
See application file for complete search history.

(56) References Cited

U.S. PATENT DOCUMENTS

2016/0334398 A1*  11/2016  Weissleder ............. G01N 21/05

OTHER PUBLICATIONS

Im et al., "Label-free detection and molecular profiling of exosomes with a nano-plasmonic sensor", 2014, Nat. Biotechnol., 32(5): 490-495 + Supplementary Information (Year: 2014).*
Wei et al., "Evaluation of the Prognostic Value of CD44 in Glioblastoma Multiforme", 2010, Anticancer Research, 30: 253-260 (Year: 2010).*
Barattin et al., "Chemical Modifications of Atomic Force Microscopy Tips", 2011, Atomic Force Microscopy in Biomedical Research, p. 457-483 (Year: 2011).*

(Continued)

*Primary Examiner* — Christopher L Chin
(74) *Attorney, Agent, or Firm* — Renner, Kenner, Greive, Bobak, Taylor & Weber

(57) ABSTRACT

A sensor for liquid biopsy, its method of making, and its method of non-invasive use. The sensor includes a substrate with a surface functionalized with biotinylated antibodies. The biotinylated antibodies are arranged to engage with surface proteins on exosomes associated with malignant cancer cells such as glioma cells.

33 Claims, 23 Drawing Sheets
(17 of 23 Drawing Sheet(s) Filed in Color)

(56) References Cited

OTHER PUBLICATIONS

Keller, S.; Schmidt, M. EGFR and EGFRvIII Promote Angiogenesis and Cell Invasion in Glioblastoma: Combination Therapies for an Effective Treatment. Int. J. Mol. Sci. 2017, 18 (6), 1295. https://doi.org/10.3390/ijms18061295.

Huang, K.; Fang, C.; Yi, K.; Liu, X.; Qi, H.; Tan, Y.; Zhou, J.; Li, Y.; Liu, M.; Zhang, Y.; et al. The Role of PTRF/Cavin1 as a Biomarker in Both Glioma and Serum Exosomes. Theranostics 2018, 8 (6), 1540-1557. https://doi.org/10.7150/thno.22952.

Figueroa, J. M.; Skog, J.; Akers, J.; Li, H.; Komotar, R.; Jensen, R.; Ringel, F.; Yang, I.; Kalkanis, S.; Thompson, R.; et al. Detection of Wild-Type EGFR Amplification and EGFRvIII Mutation in CSF-Derived Extracellular Vesicles of Glioblastoma Patients. Neuro. Oncol. 2017, 19 (11), 1494-1502. https://doi.org/10.1093/neuonc/nox085.

Ransom, C. B .; O'Neal, J. T.; Sontheimer, H. Volume-Activated Chloride Currents Contribute to the Resting Conductance and Invasive Migration of Human Glioma Cells. J. Neurosci. 2001, 21 (19), 7674-7683. https://doi.org/10.1523/JNEUROSCI.21-19-07674.2001.

Qiu, G.; Ng, S. P.; Wu, C. M. L. Differential Phase-Detecting Localized Surface Plasmon Resonance Sensor with Self-Assembly Gold Nano-Islands. Opt. Lett. 2015, 40 (9), 1924. https://doi.org/10.1364/OL.40.001924.

Qiu, G.; Ng, S. P.; Wu, L. C.-M. Dielectric Functionalization for Differential Phase Detecting Localized Surface Plasmon Resonance Biosensor. Sensors Actuators B Chem. 2016, 234, 247-254. https://doi.org/10.1016/j.snb.2016.04.151.

Loo, F.-C.; Ng, S.-P.; Wu, C.-M. L.; Kong, S. K. An Aptasensor Using DNA Aptamer and White Light Common-Path SPR Spectral Interferometry to Detect Cytochrome-c for Anti-Cancer Drug Screening. Sensors Actuators B Chem. 2014, 198, 416-423. https://doi.org/10.1016/j.snb.2014.03.077.

Bano, F.; Banerji, S.; Howarth, M.; Jackson, D. G.; Richter, R. P. A Single Molecule Assay to Probe Monovalent and Multivalent Bonds between Hyaluronan and Its Key Leukocyte Receptor CD44 under Force. Sci. Rep. 2016, 6 (1), 34176. https://doi.org/10.1038/srep34176.

Hambardzumyan, D.; Bergers, G. Glioblastoma: Defining Tumor Niches. Trends in Cancer 2015, 1 (4), 252-265. https://doi.org/10.1016/j.trecan.2015.10.009.

Thakur, A.; Zou, H.; Yang, M.; Lee, Y. Abstract 3720: Augmented Loading Efficiency of Doxorubicin into Glioma-Derived Exosomes by an Integrated Microfluidic Device. Cancer Res. 2018, 78 (13 Supplement), 3720-3720. https://doi.org/10.1158/1538-7445.AM2018-3720.

Davis, M. Glioblastoma: Overview of Disease and Treatment. Clin. J. Oncol. Nurs. 2016, 20 (5), S2-S8. https://doi.org/10.1188/16.CJON.S1.2-8.

Strickland, M.; Stoll, E. A. Metabolic Reprogramming in Glioma. Front. Cell Dev. Biol. 2017, 5. https://doi.org/10.3389/fcell.2017.00043.

Agnihotri, S.; Zadeh, G. Metabolic Reprogramming in Glioblastoma: The Influence of Cancer Metabolism on Epigenetics and Unanswered Questions. Neuro. Oncol. 2016, 18 (2), 160-172. https://doi.org/10.1093/neuonc/nov125.

Garnier, D.; Renoult, O.; Alves-Guerra, M.-C.; Paris, F.; Pecqueur, C. Glioblastoma Stem-Like Cells, Metabolic Strategy to Kill a Challenging Target. Front. Oncol. 2019, 9. https://doi.org/10.3389/fonc.2019.00118.

Masui, K.; Onizuka, H.; Cavenee, W. K.; Mischel, P. S.; Shibata, N. Metabolic Reprogramming in the Pathogenesis of Glioma: Update. Neuropathology 2019, 39 (1), 3-13. https://doi.org/10.1111/neup.12535.

Liberti, M. V.; Locasale, J. W. The Warburg Effect: How Does It Benefit Cancer Cells? Trends Biochem. Sci. 2016, 41 (3), 211-218. https://doi.org/10.1016/j.tibs.2015.12.001.

Formby, B.; Stern, R. Lactate-Sensitive Response Elements in Genes Involved in Hyaluronan Catabolismbiochem. Biophys. Res. Commun. 2003, 305 (1), 203-208. https://doi.org/10.1016/S0006-291X(03)00723-X.

Merzak, A.; Koocheckpour, S.; Pilkington, G. J. CD44 Mediates Human Glioma Cell Adhesion and Invasion in Vitro. Cancer Res. 1994, 54 (15), 3988-3992.

Ariza, A.; Lopez, D.; Mate, J. L.; Isamat, M.; Musulen, E.; Pujol, M.; Ley, A.; Navas-palacios, J. Role of CD44 in the Invasiveness of Glioblastoma Multiforme and the Noninvasiveness of Meningioma: An Immunohistochemistry Study. Hum. Pathol. 1995, 26 (10), 1144-1147. https://doi.org/10.1016/0046-8177(95)90278-3.

Koochekpour, S.; Pilkington, G. J.; Merzak, A. Hyaluronic Acid/CD44H Interaction Induces Cell Detachment and Stimulates Migration and Invasion of Human Glioma Cellsin Vitro. Int. J. Cancer 1995, 63 (3), 450-454. https://doi.org/10.1002/ijc.2910630325.

Akiyama, Y.; Jung, S.; Salhia, B.; Lee, S.; Hubbard, S.; Taylor, M .; Mainprize, T.; Akaishi, K.; van Furth, W.; Rutka, J. T. Hyaluronate Receptors Mediating Glioma Cell Migration and Proliferation. J. Neurooncol. 2001, 53 (2), 115-127. https://doi.org/10.1023/A:1012297132047.

Choi, D.; Montermini, L.; Kim, D.-K.; Meehan, B.; Roth, F. P.; Rak, J. The Impact of Oncogenic EGFRvIII on the Proteome of Extracellular Vesicles Released from Glioblastoma Cells. Mol. Cell. Proteomics 2018, 17 (10), 1948-1964. https://doi.org/10.1074/mcp.RA118.000644.

Knüpfer, M. M.; Poppenborg, H.; Hotfilder, M.; Kuhnel, K.; Wolff, J. E.; Domula, M. CD44 Expression and Hyaluronic Acid Binding of Malignant Glioma Cells. Clin. Exp. Metastasis 1999, 17 (1), 71-76.

Cortes-Dericks, L.; Schmid, R. A. CD44 and Its Ligand Hyaluronan as Potential Biomarkers in Malignant Pleural Mesothelioma: Evidence and Perspectives. Respir. Res. 2017, 18 (1), 58. https://doi.org/10.1186/s12931-017-0546-5.

Misra, S.; Heldin, P.; Hascall, V. C.; Karamanos, N. K.; Skandalis, S. S.; Markwald, R. R.; Ghatak, S. Hyaluronan-CD44 Interactions as Potential Targets for Cancer Therapy. Febs J. 2011, 278 (9), 1429-1443. https://doi.org/10.1111/j.1742-4658.2011.08071.x.

Thakur, A.; Qiu, G.; Ng, S.-P.; Wu, C.-M. L.; Lee, Y. Detection of Membrane Antigens of Extracellular Vesicles by Surface Plasmon Resonance. J. Lab. Precis. Med. 2017, 2, 98-98. https://doi.org/10.21037/jlpm.2017.12.08.

Thakur, A.; Qiu, G.; Ng, S.-P.; Guan, J.; Yue, J.; Lee, Y.; Wu, C.-M. L. Direct Detection of Two Different Tumor-Derived Extracellular Vesicles by SAM-AuNIs LSPR Biosensor. Biosens. Bioelectron. 2017, 94, 400-407. https://doi.org/10.1016/j.bios.2017.03.036.

Camussi, G.; Deregibus, M. C.; Bruno, S.; Cantaluppi, V.; Biancone, L. Exosomes/Microvesicles as a Mechanism of Cell-to-Cell Communication. Kidney Int. 2010, 78 (9), 838-848. https://doi.org/10.1038/ki.2010.278.

Kucharzewska, P.; Christianson, H. C.; Welch, J. E.; Svensson, K. J.; Fredlund, E.; Ringner, M.; Morgelin, M.; Bourseau-Guilmain, E.; Bengzon, J.; Belting, M. Exosomes Reflect the Hypoxic Status of Glioma Cells and Mediate Hypoxia-Dependent Activation of Vascular Cells during Tumor Development. Proc. Natl. Acad. Sci. 2013, 110 (18), 7312-7317. https://doi.org/10.1073/pnas.1220998110.

Lang, H.-L.; Hu, G.-W.; Zhang, B.; Kuang, W.; Chen, Y.; Wu, L.; Xu, G.-H. Glioma Cells Enhance Angiogenesis and Inhibit Endothelial Cell Apoptosis through the Release of Exosomes That Contain Long Non-Coding RNA CCAT2. Oncol. Rep. 2017, 38 (2), 785-798. https://doi.org/10.3892/or.2017.5742.

García-Romero, N.; Carrión-Navarro, J.; Esteban-Rubio, S.; Lázaro-Ibáñez, E.; Peris-Celda, M.; Alonso, M. M.; Guzmán-De-Villoria, J.; Fernández-Carballal, C.; de Mendivil, A. O.; Garcia-Duque, S.; et al. DNA Sequences within Glioma-Derived Extracellular Vesicles Can Cross the Intact Blood-Brain Barrier and Be Detected in Peripheral Blood of Patients. Oncotarget 2017, 8 (1). https://doi.org/10.18632/oncotarget.13635.

Li, A.; Zhang, T.; Zheng, M.; Liu, Y.; Chen, Z. Exosomal Proteins as Potential Markers of Tumor Diagnosis. J. Hematol. Oncol. 2017, 10 (1), 175. https://doi.org/10.1186/s13045-017-0542-8.

(56) References Cited

OTHER PUBLICATIONS

Lan, H.; Lu, H.; Wang, X.; Jin, H. MicroRNAs as Potential Biomarkers in Cancer: Opportunities and Challenges. Biomed Res. Int. 2015, 2015, 1-17. https://doi.org/10.1155/2015/125094.
Sina, A. A. I.; Vaidyanathan, R.; Dey, S.; Carrascosa, L. G.; Shiddiky, M. J. A.; Trau, M. Real Time and Label Free Profiling of Clinically Relevant Exosomes. Sci. Rep. 2016, 6 (1), 30460. https://doi.org/10.1038/srep30460.
Im, H.; Lee, K.; Weissleder, R.; Lee, H.; Castro, C. M. Novel Nanosensing Technologies for Exosome Detection and Profiling. Lab Chip 2017, 17 (17), 2892-2898. https://doi.org/10.1039/C7LC00247E.
Qiu, G.; Thakur, A.; Xu, C.; Ng, S.-P.; Lee, Y.; Wu, C.-M. L. Detection of Glioma-Derived Exosomes with the Biotinylated Antibody-Functionalized Titanium Nitride Plasmonic Biosensor. Adv. Funct. Mater. 2019, 29 (9), 1806761. https://doi.org/10.1002/adfm.201806761.
Grasso, L.; Wyss, R.; Weidenauer, L.; Thampi, A.; Demurtas, D.; Prudent, M.; Lion, N.; Vogel, H. Molecular Screening of Cancer-Derived Exosomes by Surface Plasmon Resonance Spectroscopy. Anal. Bioanal. Chem. 2015, 407 (18), 5425-5432. https://doi.org/10.1007/s00216-015-8711-5.
Qiu, G.; Ng, S. P.; Wu, C.-M. L. Label-Free Surface Plasmon Resonance Biosensing with Titanium Nitride Thin Film. Biosens. Bioelectron. 2018, 106, 129-135. https://doi.org/10.1016/j.bios.2018.02.006.
Kwizera, E. A.; O'Connor, R.; Vinduska, V.; Williams, M.; Butch, E. R.; Snyder, S. E.; Chen, X.; Huang, X. Molecular Detection and Analysis of Exosomes Using Surface-Enhanced Raman Scattering Gold Nanorods and a Miniaturized Device. Theranostics 2018, 8 (10), 2722-2738. https://doi.org/10.7150/thno.21358.
Kaur, V.; Singh, S. Design of Titanium Nitride Coated PCF-SPR Sensor for Liquid Sensing Applications. Opt. Fiber Technol. 2019, 48, 159-164. https://doi.org/10.1016/j.yofte.2018.12.015.
Gautier, H. O. B.; Thompson, A. J.; Achouri, S.; Koser, D. E.; Holtzmann, K.; Moeendarbary, E.; Franze, K. Atomic Force Microscopy-Based Force Measurements on Animal Cells and Tissues. In Methods Cell Biol.; 2015; pp. 211-235. https://doi.org/10.1016/bs.mcb.2014.10.005.
Sharma, S.; Rasool, H. I.; Palanisamy, V.; Mathisen, C.; Schmidt, M.; Wong, D. T.; Gimzewski, J. K. Structural-Mechanical Characterization of Nanoparticle Exosomes in Human Saliva, Using Correlative AFM, FESEM, and Force Spectroscopy. ACS Nano 2010, 4 (4), 1921-1926. https://doi.org/10.1021/nn901824n.
Stylianou, A.; Kontomaris, S.-V.; Grant, C.; Alexandratou, E. Atomic Force Microscopy on Biological Materials Related to Pathological Conditions. Scanning 2019, 2019, 1-25. https://doi.org/10.1155/2019/8452851.
Sharma, S.; Gillespie, B. M.; Palanisamy, V.; Gimzewski, J. K. Quantitative Nanostructural and Single-Molecule Force Spectroscopy Biomolecular Analysis of Human-Saliva-Derived Exosomes. Langmuir 2011, 27 (23), 14394-14400. https://doi.org/10.1021/la2038763.
Li, M.; Xiao, X.; Liu, L.; Xi, N.; Wang, Y.; Dong, Z.; Zhang, W. Nanoscale Mapping and Organization Analysis of Target Proteins on Cancer Cells from B-Cell Lymphoma Patients. Exp. Cell Res. 2013, 319 (18), 2812-2821. https://doi.org/10.1016/j.yexcr.2013.07.020.
Li, M.; Dang, D.; Liu, L.; Xi, N.; Wang, Y. Imaging and Force Recognition of Single Molecular Behaviors Using Atomic Force Microscopy. Sensors 2017, 17 (12), 200. https://doi.org/10.3390/s17010200.
Soares Martins, T.; Catita, J.; Martins Rosa, I.; A. B. da Cruz e Silva, O.; Henriques, A. G. Exosome Isolation from Distinct Biofluids Using Precipitation and col. Based Approaches. PLoS One 2018, 13 (6), e0198820. https://doi.org/10.1371/journal.pone.0198820.
Shlyakhtenko, L. S.; Gall, A. A.; Lyubchenko, Y. L. Mica Functionalization for Imaging of DNA and Protein-DNA Complexes with Atomic Force Microscopy; 2012; pp. 295-312. https://doi.org/10.1007/978-1-62703-056-4_14.
Chada, N.; Sigdel, K. P.; Gari, R. R. S.; Matin, T. R.; Randall, L. L.; King, G. M. Glass Is a Viable Substrate for Precision Force Microscopy of Membrane Proteins. Sci. Rep. 2015, 5 (1), 12550. https://doi.org/10.1038/srep12550.
El Kirat, K.; Burton, I.; Dupres, V.; Dufrene, Y. F. Sample Preparation Procedures for Biological Atomic Force Microscopy. J. Microsc. 2005, 218 (3), 199-207. https://doi.org/10.1111/j.1365-2818.2005.01480.x.
Pürckhauer, K.; Weymouth, A. J.; Pfeffer, K.; Kullmann, L.; Mulvihill, E.; Krahn, M. P.; Muller, D. J.; Giessibl, F. J. Imaging in Biologically-Relevant Environments with AFM Using Stiff QPlus Sensors. Sci. Rep. 2018, 8 (1), 9330. https://doi.org/10.1038/s41598-018-27608-6.
Esslinger, M.; Dorfmüller, J.; Khunsin, W.; Vogelgesang, R.; Kern, K. Background-Free Imaging of Plasmonic Structures with Cross-Polarized Apertureless Scanning near-Field Optical Microscopy. Rev. Sci. Instrum. 2012, 83 (3), 033704. https://doi.org/10.1063/1.3693346.
Baumann, F.; Leukel, P.; Doerfelt, A.; Beier, C. P.; Dettmer, K.; Oefner, P. J.; Kastenberger, M.; Kreutz, M.; Nickl-Jockschat, T.; Bogdahn, U.; et al. Lactate Promotes Glioma Migration by TGF-B2-Dependent Regulation of Matrix Metalloproteinase-2. Neuro. Oncol. 2009, 11 (4), 368-380. https://doi.org/10.1215/15228517-2008-106.
Taylor, D. D.; Gercel-Taylor, C. MicroRNA Signatures of Tumor-Derived Exosomes as Diagnostic Biomarkers of Ovarian Cancer. Gynecol. Oncol. 2008, 110 (1), 13-21. https://doi.org/10.1016/j.ygyno.2008.04.033.
Rosell, R.; Wei, J.; Taron, M. Circulating MicroRNA Signatures of Tumor-Derived Exosomes for Early Diagnosis of Non-Small-Cell Lung Cancer. Clin. Lung Cancer 2009, 10 (1), 8-9. https://doi.org/10.3816/CLC.2009.n.001.
San-Millán, I.; Brooks, G. A. Reexamining Cancer Metabolism: Lactate Production for Carcinogenesis Could Be the Purpose and Explanation of the Warburg Effect. Carcinogenesis 2016, bgw127. https://doi.org/10.1093/carcin/bgw127.
Stern, R.; Shuster, S .; Neudecker, B. A.; Formby, B. Lactate Stimulates Fibroblast Expression of Hyaluronan and CD44: The Warburg Effect Revisited. Exp. Cell Res. 2002, 276 (1), 24-31. https://doi.org/10.1006/excr.2002.5508.
Allison, D. P.; Mortensen, N. P.; Sullivan, C. J.; Doktycz, M. J. Atomic Force Microscopy of Biological Samples. Wiley Interdiscip. Rev. Nanomedicine Nanobiotechnology 2010, 2 (6), 618-634. https://doi.org/10.1002/wnan.104.

* cited by examiner

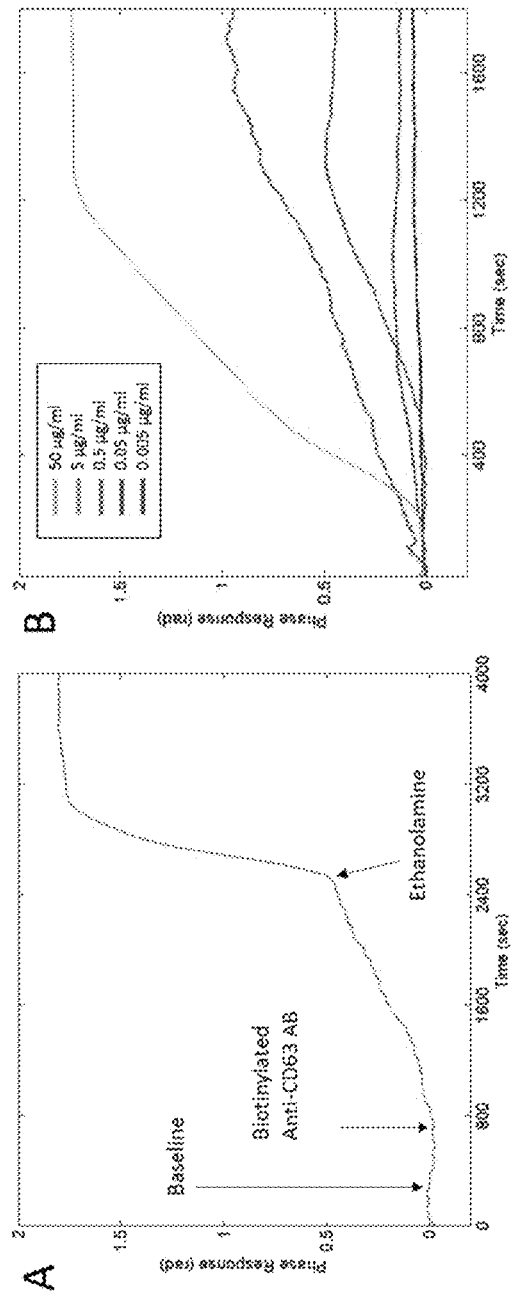
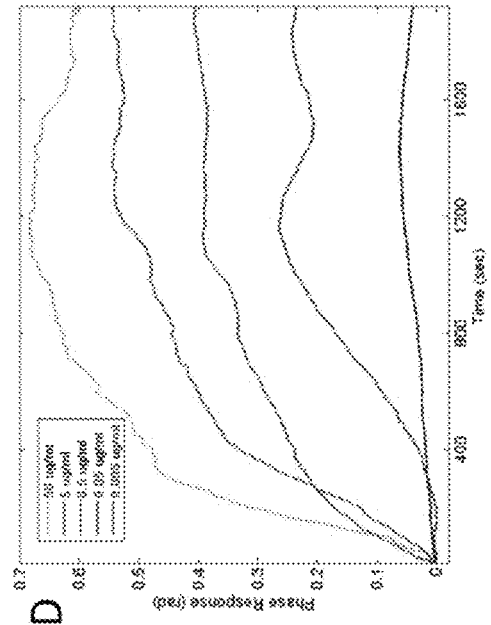
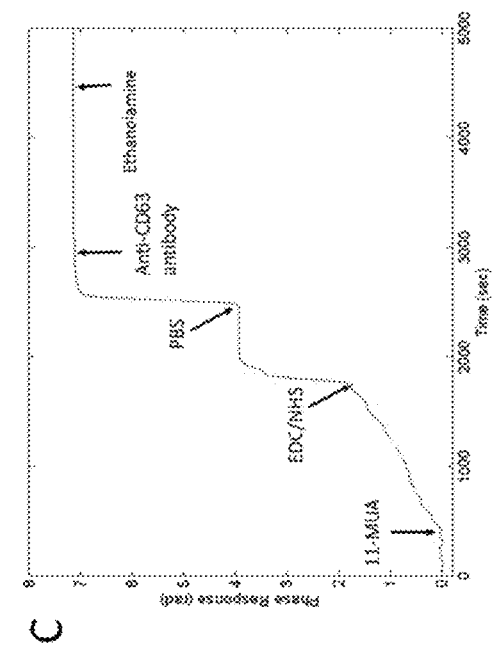
Figure 5A
Figure 5B
Figure 5C
Figure 5D

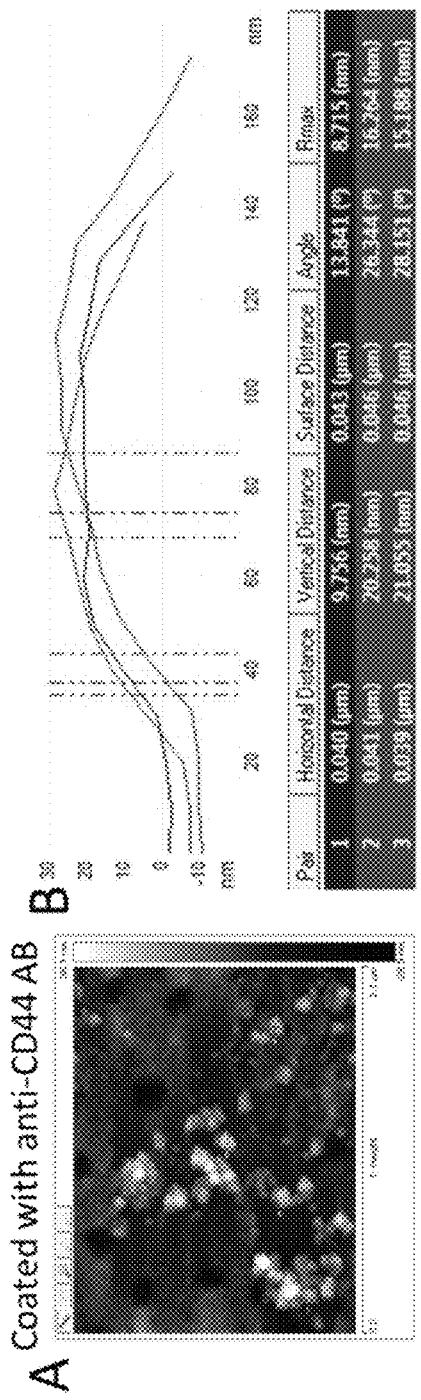
Figure 7A
Figure 7B
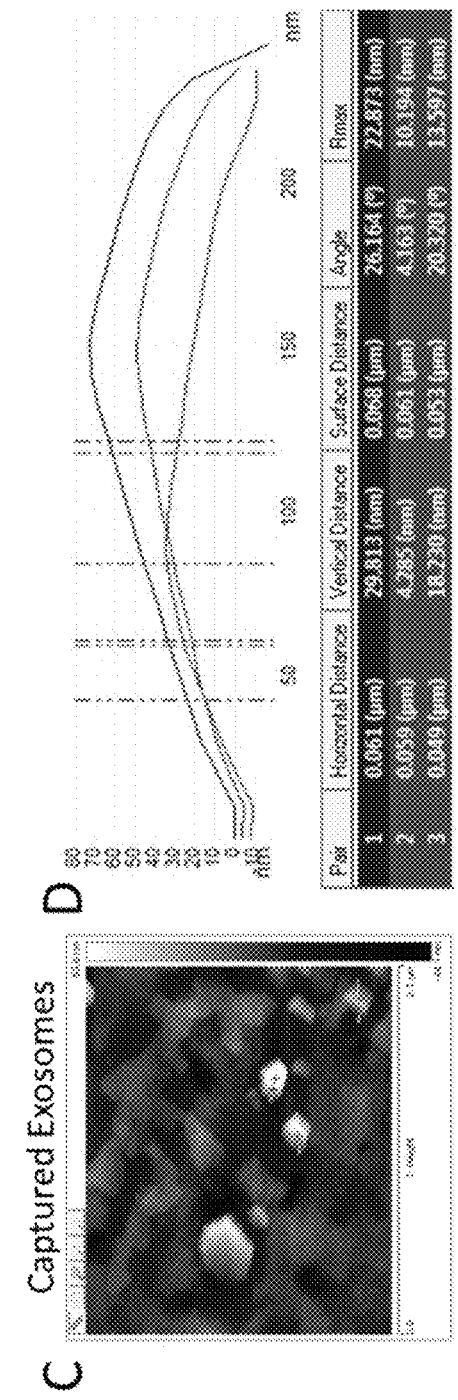
Figure 7C
Figure 7D

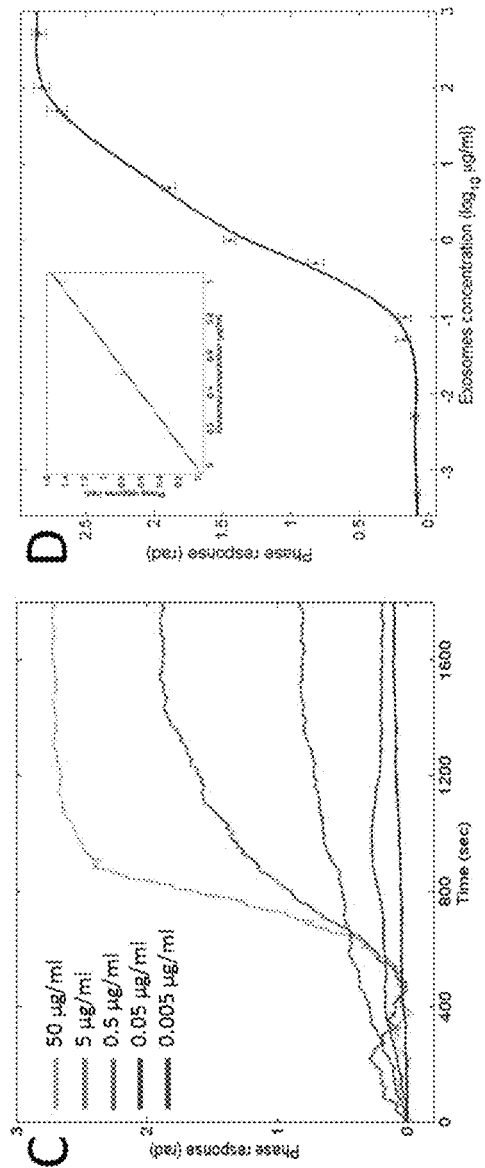
Figure 9C
Figure 9D
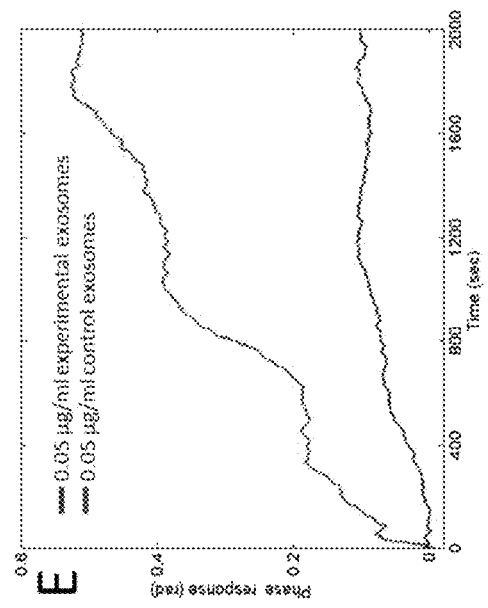
Figure 9E

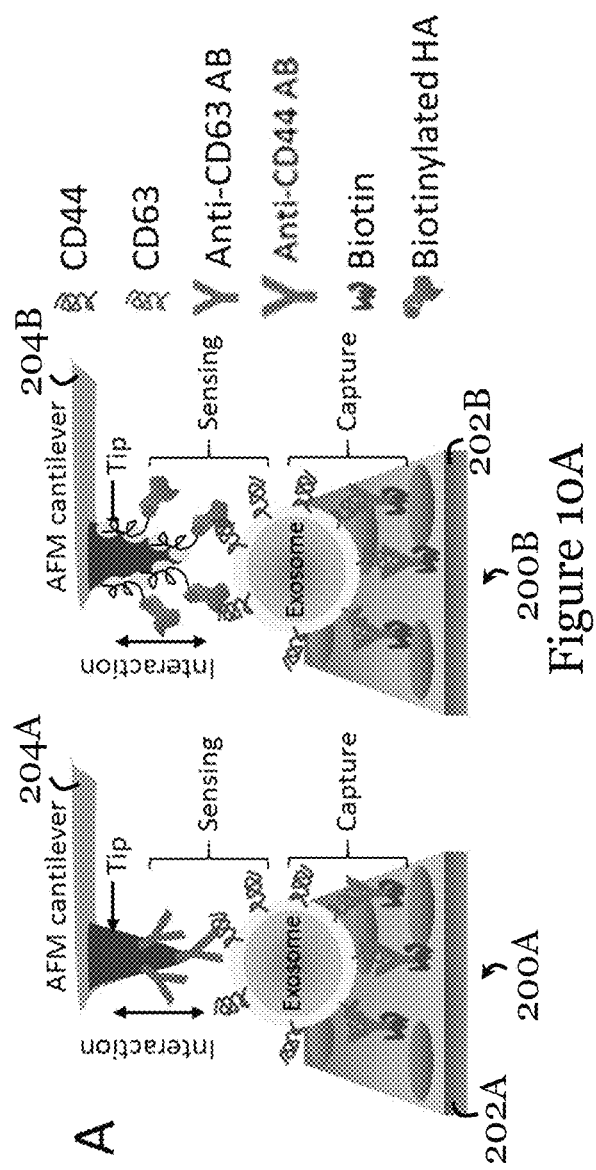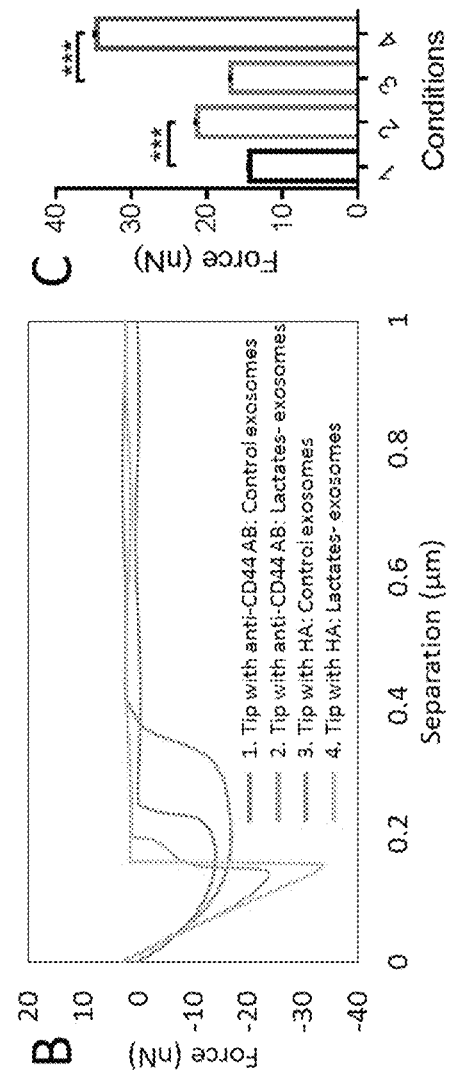
Figure 10A
Figure 10B
Figure 10C

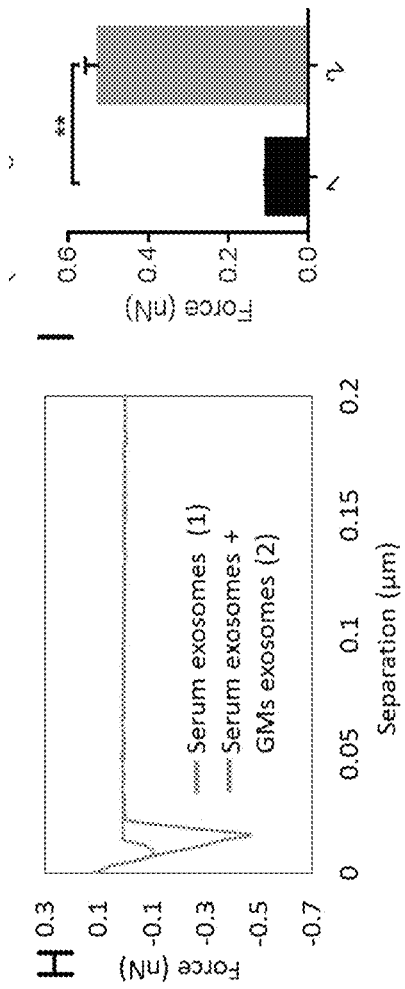
Figure 11F
Figure 11G
Figure 11H
Figure 11I

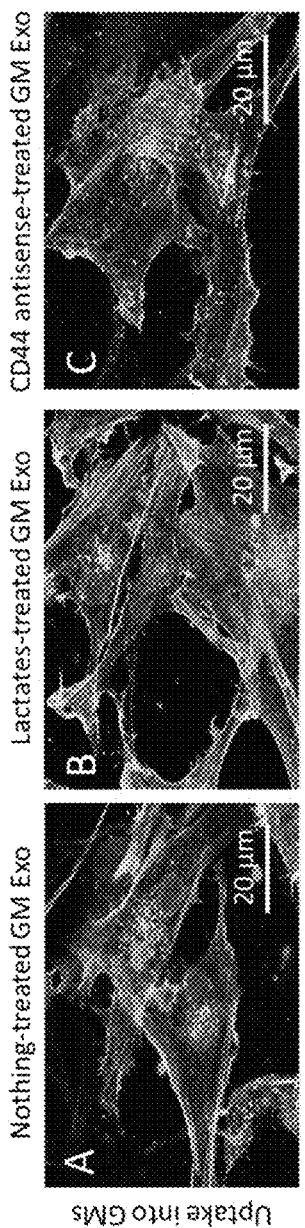
Figure 12A  Figure 12B  Figure 12C  Figure 12D  Figure 12E  Figure 12F

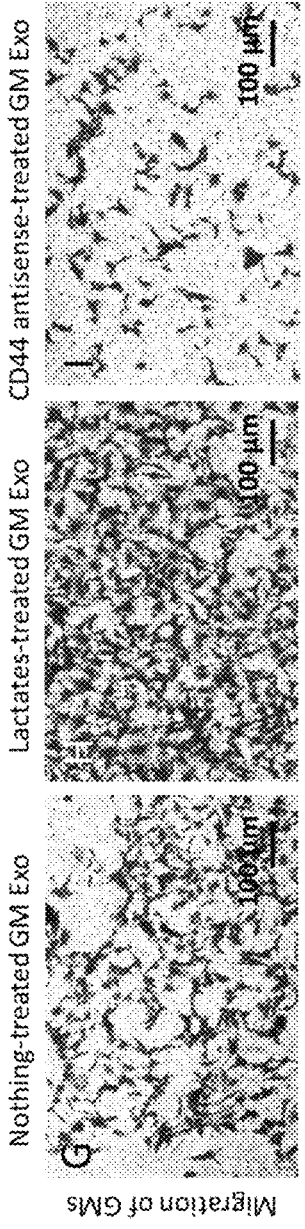
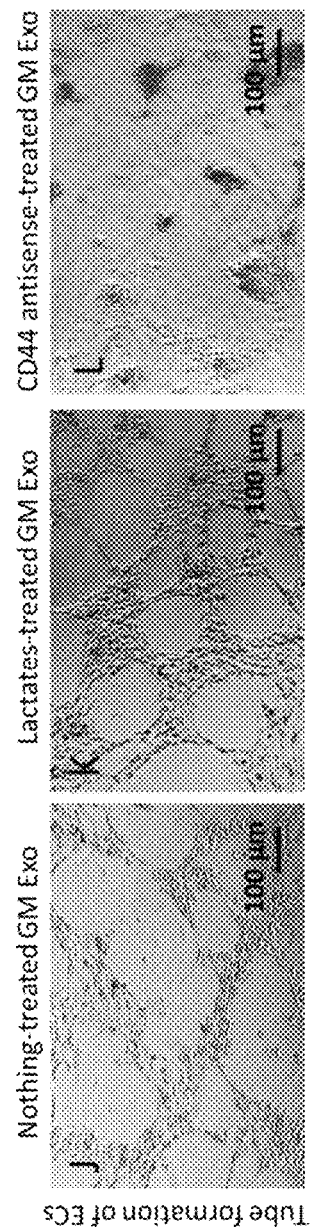
Figure 12G Figure 12H Figure 12I Figure 12J Figure 12K Figure 12L

SENSOR FOR LIQUID BIOPSY AND ITS METHOD OF MAKING, AND METHOD OF NON-INVASIVE LIQUID BIOPSY

TECHNICAL FIELD

The invention relates to a sensor for liquid biopsy, a method of making such sensor, and a method of using such sensor for non-invasive liquid biopsy.

BACKGROUND

Conventional diagnosis and prognosis of cancers such as glioma utilize magnetic resonance imaging (MRI), computed tomography (CT) scans, and intracranial biopsies. However, the requirement of detection of precise molecular signature of glioma progression and metabolic adaptation has not been satisfactorily met. Thus, the development of additional diagnostic tools with precise biomarkers is needed, synergistically with currently available tools, to monitor the progression of malignant cancers such as glioma.

Depending on the applications and needs, extracellular vesicles (EVs), including exosomes and micro-vesicles (MVs), can be characterized using different techniques and tools. These techniques and tools include nanoparticle tracking analysis (NTA), dynamic light scattering (DLS), scanning electron microscopy (SEM), transmission electron microscopy (TEM), cryo-electron microscopy (cryo-EM), immunogold electron microscopy (immunogold EM), flow cytometry, western blotting, and enzyme-linked immunosorbent assay (ELISA). These methods can be used to obtain respective useful information about extracellular vesicles such as exosomes, but they each have their own limitation(s).

There remains a need for improved or alternative techniques that can non-invasively and precisely detect exosomes and exosomal proteins for study or characterization of cancers such as glioma.

SUMMARY OF THE INVENTION

In accordance with a first aspect of the invention, there is provided a sensor for liquid biopsy. The sensor includes a substrate with a surface functionalized with biotinylated antibodies. The biotinylated antibodies are arranged to engage with surface proteins on exosomes associated with malignant cancer cells.

In one embodiment of the first aspect, the exosomes are released by the malignant cancer cells.

In one embodiment of the first aspect, the malignant cancer cells are glioma cells.

In one embodiment of the first aspect, the biotinylated antibodies include biotinylated anti-CD63 antibodies.

In one embodiment of the first aspect, the biotinylated antibodies include biotinylated anti-CD44 antibodies.

In one embodiment of the first aspect, the biotinylated antibodies include biotinylated anti-EGFRvIII antibodies.

In one embodiment of the first aspect, the biotinylated antibodies include one or more (or all) of: biotinylated anti-CD63 antibodies, biotinylated anti-CD44 antibodies, and biotinylated anti-EGFRVIII antibodies.

The substrate and the surface may be made of the same material. Alternatively, the substrate and the surface may be made of different materials.

In one embodiment of the first aspect, the surface is made of plasmonic material. The plasmonic material may include titanium nitride or titanium nitride-based material.

In one embodiment of the first aspect, the substrate is in the form of a nanofilm of titanium nitride or titanium nitride-based material.

In one embodiment of the first aspect, the surface is in the form of a nanofilm of titanium nitride or titanium nitride-based material.

In one embodiment of the first aspect, the surface comprises nano-holes.

In one embodiment of the first aspect, the substrate is in the form of a chip or a disc.

In one embodiment of the first aspect, the sensor further includes: a housing defining a space, the substrate being arranged in the space; an inlet; and an outlet. The inlet, the outlet, and the space are in liquid communication with each other.

In one embodiment of the first aspect, the sensor further includes: a cantilever for atomic force microscopy. The cantilever is arranged to be operably cooperating with the substrate. The cantilever includes a tip with a tip surface functionalized with biotinylated antibodies complementary to surface proteins on the exosomes. The biotinylated antibodies on the tip surface may include biotinylated anti-CD44 antibodies arranged to engage with CD44 on the surface of the exosomes. The biotinylated antibodies on the tip surface may alternatively or additionally include anti-CD63 antibodies arranged to engage with CD63 on the surface of the exosomes and/or anti-EGFRVIII antibodies arranged to engage with EGFRVIII on the surface of the exosomes.

In one embodiment of the first aspect, the sensor further includes: a cantilever for atomic force microscopy. The cantilever is arranged to be operably cooperating with the substrate. The cantilever includes a tip with a tip surface functionalized with biotinylated hyaluronic acid complementary to surface proteins on the exosomes. The biotinylated hyaluronic acid is arranged to engage with CD44 on the surface of the exosomes.

In accordance with a second aspect of the invention, there is provided a method of non-invasive liquid biopsy. The method includes providing a solution containing exosomes associated with malignant cancer cells to a substrate with a surface functionalized with biotinylated antibodies. The biotinylated antibodies are arranged to engage with surface proteins on the exosomes associated with malignant cancer cells. The method also includes detecting exosomes engaged with the surface of the substrate.

In one embodiment of the second aspect, the method further includes determining a severity of the malignant cancer based on the detection. Determining the severity may include determining the progression of the cancer, characterizing the stage of the cancer, etc.

In one embodiment of the second aspect, the method further includes performing localized surface plasmon resonance spectroscopy using the substrate engaged with the exosomes.

In one embodiment of the second aspect, the method further includes performing atomic force microscopy using the substrate engaged with the exosomes.

In one embodiment of the second aspect, the exosomes are released by the malignant cancer cells.

In one embodiment of the second aspect, the malignant cancer cells are glioma cells.

In one embodiment of the second aspect, the biotinylated antibodies include one or more of: biotinylated anti-CD63 antibodies, biotinylated anti-CD44 antibodies, and biotinylated anti-EGFRVIII antibodies.

In accordance with a third aspect of the invention, there is provided a method for non-invasive liquid biopsy using the sensor of the first aspect. The method may be the method of the second aspect.

In accordance with a fourth aspect of the invention, there is provided a method for making a sensor for liquid biopsy. The method includes providing a substrate with a surface; and functionalizing the surface with biotinylated antibodies. The biotinylated antibodies are arranged to engage with surface proteins on exosomes associated with malignant cancer cells.

In one embodiment of the fourth aspect, the exosomes are released by the malignant cancer cells.

In one embodiment of the fourth aspect, the malignant cancer cells are glioma cells.

In one embodiment of the fourth aspect, the biotinylated antibodies may include one or more or all of: biotinylated anti-CD63 antibodies, biotinylated anti-CD44 antibodies, and biotinylated anti-EGFRvIII antibodies.

In one embodiment of the fourth aspect, the surface is made of plasmonic material.

In one embodiment of the fourth aspect, the plasmonic material comprises titanium nitride or titanium nitride-based material.

In one embodiment of the fourth aspect, the surface comprises nano-holes.

In one embodiment of the fourth aspect, the method also includes forming the substrate with the surface.

In one embodiment of the fourth aspect, forming the substrate includes: depositing a film made of gold on a glass substrate; annealing the glass substrate with deposited gold film such that the gold film at least partly becomes gold nano-islands that are at least partly received in the glass substrate; deposit a firm of titanium nitride or titanium nitride-based material on the annealed glass substrate with gold nano-islands; and removing the gold nano-islands.

In one embodiment of the fourth aspect, the annealing is performed for around 9 hours at 500 to 600 degree-Celsius.

In one embodiment of the fourth aspect, the removal of the gold nano-islands is by immersion to a gold-dissolved solution (e.g., AN-50 solution).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the invention will now be described, by way of example, with reference to the accompanying drawings in which:

FIG. 5A is a graph showing the localized surface plasmon resonance phase response of the TIN-NH chip in the process of functionalization with biotinylated anti-CD63 antibodies in one example of the invention;

FIG. 5B is a graph showing the localized surface plasmon resonance phase response of U87 glioma cells-derived exosomes toward the functionalized TiN—NH chip for different concentrations of exosomes;

FIG. 5C is a graph showing the localized surface plasmon resonance phase response of the AuNI chip in the process of functionalization with anti-CD63 antibodies in one example of the invention;

FIG. 5D is a graph showing localized surface plasmon resonance phase response of U87 glioma cells-derived exosomes toward the functionalized AuNI chip for different concentrations of exosomes;

FIG. 7A is a peak force atomic force microscopy topographic image of a TiN—NH chip coated with anti-CD44 antibodies in 2D (2.1 μm×2.1 μm) in one example of the invention;

FIG. 7B is graph showing the height profile of the surface of TiN—NH chip in FIG. 7A;

FIG. 7C is a peak force atomic force microscopy topographic image of a TiN—NH chip coated with anti-CD44 antibodies in 2D (2.1 μm×2.1 μm), with captured U87 glioma cells-derived exosomes, in one example of the invention;

FIG. 7D is graph showing the height profile of the surface of the TIN-NH chip in FIG. 7C;

FIG. 9C is a graph showing the localized surface plasmon resonance phase response of glioma cells-derived exosomes toward the functionalized TiN—NH chip with anti-CD44 antibodies;

FIG. 9D is a graph showing a corresponding calibration curve revealing the correlation between the localized surface plasmon resonance phase response and the quantity of exosomes;

FIG. 9E is a graph showing the localized surface plasmon resonance phase response of exosomes from U87 glioma cells with (experimental group) and without (control) lactate treatment toward the functionalized TiN—NH chip with anti-CD44 antibodies;

FIG. 10A is a schematic diagram illustrating sensors for capturing exosomal CD63 and, cooperating with the sensors, atomic force microscopy cantilever tip for detecting exosomal CD44 or hyaluronic acid;

FIG. 10B is a graph showing separation force measurement obtained by atomic force microscopy revealing the differential adhesion force between anti-CD44 antibodies or hyaluronic acid and CD44 in exosomes from glioma cells, both with and without (control) lactate treatment;

FIG. 10C is a bar graph showing the comparison of adhesion force between groups 1-4 labeled in FIG. 10B;

FIG. 11F is a graph showing atomic force microscopy force curves illustrating differential adhesion force between anti-CD44 antibodies on the tip and CD44 in U87 glioma cells-derived exosomes captured by anti-EGFRVIII antibodies on the TIN-NH discs (as compared to the control);

FIG. 11G is a bar graph summarizing the relative strength of the different exosomes in FIG. 11F;

FIG. 11H is a graphs showing atomic force microscopy force curves illustrating differential adhesion force between anti-CD44 antibodies on the tip and CD44 in U87 glioma cells-derived exosomes captured by anti-EGFRVIII antibodies on the TiN—NH discs from their mixture with serum-derive exosomes (as compared to the control);

FIG. 11I is a bar graph summarizing the relative strength of the different exosomes in FIG. 11H;

FIG. 12A is an immunofluorescent image (Blue: DAPI, Red: Phalloidin, Green: Exo-Green) of autologous uptake of exosomes from the glioma cells without treatment of 40 mM lactate into glioma cells or endothelial cells;

FIG. 12B is an immunofluorescent image (Blue: DAPI, Red: Phalloidin, Green: Exo-Green) of autologous uptake of exosomes from the glioma cells with treatment of 40 mM lactate into glioma cells or endothelial cells;

FIG. 12C is an immunofluorescent image (Blue: DAPI, Red: Phalloidin, Green: Exo-Green) of autologous uptake of exosomes from the glioma cells with treatment of CD44-antisense LNA GapmeR oligonucleotides into glioma cells or endothelial cells;

FIG. 12D is an immunofluorescent image (Blue: DAPI, Red: Phalloidin, Green: Exo-Green) of heterologous uptake of exosomes from the glioma cells without treatment of 40 mM lactate into glioma cells or endothelial cells;

FIG. 12E is an immunofluorescent image (Blue: DAPI, Red: Phalloidin, Green: Exo-Green) of heterologous uptake of exosomes from the glioma cells with treatment of 40 mM lactate into glioma cells or endothelial cells;

FIG. 12F is an immunofluorescent image (Blue: DAPI, Red: Phalloidin, Green: Exo-Green) of heterologous uptake of exosomes from the glioma cells with treatment of CD44-antisense LNA GapmeR oligonucleotides into glioma cells or endothelial cells;

FIG. 12G is an image showing the effect of autologous uptake (migration of glioma cells) corresponding to FIG. 12A;

FIG. 12H is an image showing the effect of autologous uptake (migration of glioma cells) corresponding to FIG. 12B;

FIG. 12I is an image showing the effect of autologous uptake (migration of glioma cells) corresponding to FIG. 12C;

FIG. 12J is an image showing the effect of heterologous uptake (tube formation of endothelial cells) corresponding to FIG. 12D;

FIG. 12K is an image showing the effect of heterologous uptake (tube formation of endothelial cells) corresponding to FIG. 12E;

FIG. 12L is an image showing the effect of heterologous uptake (tube formation of endothelial cells) corresponding to FIG. 12F;

DETAILED DESCRIPTION

Figure 1:
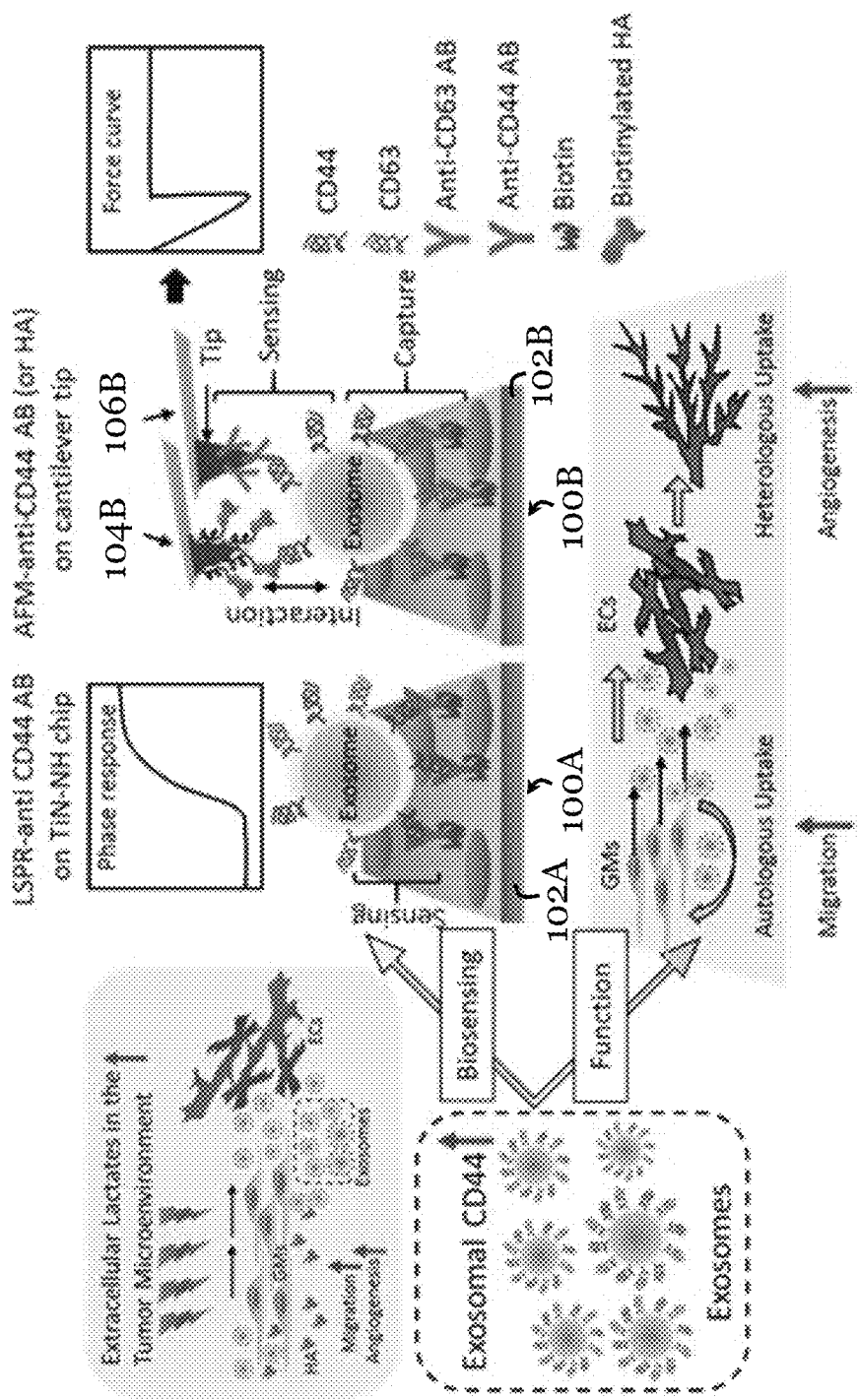
FIG. 1 is a schematic diagram illustrating the function of exosomal CD44 and the sensing of exosomal CD44 using the sensors in one embodiment of the invention to track the malignant progression of glioma cells as a biomarker.

The inventors of the present invention have devised, through research, experiments, and/or trials, that one of the most detrimental tumors in the central nervous system (CNS) is malignant glioma. In general, the progression of malignant glioma can be characterized by the increased migration and invasion of glioma cells as well as the enhanced tube formation of endothelial cells (ECs) in the tumor microenvironment. While the combinatorial treatment against malignant glioma using chemotherapy, radiation, and surgical removal may be useful, the average survival of patients with malignant glioma is still only one and a half years partly because of difficulty in its diagnosis at an early stage. The inventors of the present invention have devised, through research, experiments, and/or trials, that the glycolytic reprogramming of glioma cells is closely related to their metastasis and invasion via both facilitating phenotypic transition and inducing drug resistance in cancer therapy. As a result of glycolysis, malignant glioma cells produce tremendous amount of lactate that is released into the tumor microenvironment, even with enough oxygen supply, known as the "Warburg effect". Increased lactate in the tumor microenvironment have been shown to diffuse into tumor associated fibroblasts capable of the synthesis of hyaluronic acid, leading to the adhesion of glioma cells to each other and to ECs as well as the reorganization of the extracellular matrix which is necessary for tumor progression. Lactate can upregulate CD44 in glioma cells, a cell surface adhesion molecule, which is associated with cell migration and invasion via the interaction with its ligand, hyaluronic acid in the tumor microenvironment. Particularly, glioma cells, expressing epidermal growth factor receptor variant-III (EGFRVIII), have significant amount of CD44 in the membrane of filopodia, promoting their motility and migration. Therefore, it is believed that the level of hyaluronic acid, CD44, and their interactions are a close positive correlation with tumor severity, both hyaluronic acid and CD44 can be faithful biomarkers to track tumor malignancy, and the inhibitors for hyaluronic acid-CD44 interactions can be anticancer agents.

Exosomes, one of the smallest types of cell-derived extracellular vesicles (EVs) with an exemplary average size range of 30-200 nm, are present in most biological fluids including blood, cerebrospinal fluid (CSF), saliva, and urine. They have been recognized as the major messenger vehicle playing a crucial role in cell-cell communication in both normal condition and pathological condition (such as brain cancer). The inventors of the present invention have devised, through research, experiments, and/or trials, that malignant cancer cells, including glioma cells, release remarkably high amount of exosomes into the tumor microenvironment, leading to the support of tumor progression by enhancing the autologous and heterologous interactions with surrounding cells, and particularly, glioma cells-derived exosomes, which can cross the blood-brain-barrier and the blood-CSF barrier, may be utilized as a non-invasive biomarker discovery platform to track the malignant progression of parent glioma cells, such as migration and invasion. Molecular profiling analyses have demonstrated that exosomal components, including exosomal microRNA and proteins, can be good supporting biomarkers in determining tumor malignancy. Nonetheless, non-invasive label-free techniques through biosensing of exosomal surface components may be used in the diagnosis and prognosis in cancer as a liquid biopsy because of their capability of simple quantitative detection of surface proteins associated with a specific type of cancer and its progression.

FIG. 1 is a schematic diagram illustrating the function of exosomal CD44 and the sensing of exosomal CD44 using the sensors in one embodiment of the invention to track the malignant progression of glioma cells as a biomarker. As shown in FIG. 1, glioma cells in the tumor microenvironment can utilize increased extracellular lactate for their adaptation and survival partly by the upregulation of CD44 expression and exosome release. This does not only make them more malignant but also enables surrounding ECs to be more angiogenic. Enhanced exosomal CD44 released from malignant glioma cells can be effectively detected by the sensors 100A, 100B as illustrated, which are sensitive and non-invasive, and can be used for liquid biopsies for glioma.

One of the sensors 100A includes a titanium nitride nano-holes (TiN—NH) chip 102A with a surface functionalized with biotinylated anti-CD44 antibodies. The surface (and optionally the entire chip 102A) can be made with titanium nitride or titanium nitride-based material. The biotinylated anti-CD44 antibodies are arranged to engage with CD44 on the surface of exosomes associated with the glioma cells. The sensor 100A, with captured exosomes, can be used for localized surface plasmon resonance (LSPR) analysis (e.g., microscopy), to obtain phase response which relates to, e.g., the amount of captured exosomes, which indirectly reflect the progression of glioma. In one implementation (not specifically shown), the chip 102A can be placed in a housing with an inlet and an outlet so that the solution (biofluid sample obtained from patient) can be passed from the inlet through the chip 102A to the outlet for liquid biopsy. In the following this sensor 100A may be referred to as titanium nitride-nano-holes-localized surface plasmon resonance (TIN-NH-LSPR) biosensor.

Another one of the sensors 100B includes a titanium nitride nano-holes (TiN—NH) chip 102B with a surface functionalized with biotinylated anti-CD63 antibodies. The biotinylated anti-CD63 antibodies are arranged to engage with CD63 on the surface of exosomes associated with the glioma cells. The sensor 100B also includes one or both of the cantilevers 104B, 106B for atomic force microscopy. The cantilevers 104B, 106B are each arranged to operably cooperate with the chip 102B. The cantilever 104B has a tip with a tip surface functionalized with biotinylated hyaluronic acid. The biotinylated hyaluronic acid is arranged to engage with CD44 on the surface of exosomes associated with the glioma cells. On the other hand, the cantilever 106B has a tip with a tip surface functionalized with biotinylated anti-CD44 antibodies. The biotinylated anti-CD44 antibodies are arranged to engage with CD44 on the surface of exosomes associated with the glioma cells, for performing atomic force microscopy. In the following this sensor 100B may be referred to as titanium nitride-nano-holes-discs immunocapture-atomic force microscopy (TIC-AFM) biosensor.

Extracellular Lactate Promotes Migration of Glioma Cells Via CD44

One important phenomenon that malignant glioma cells may undergo is enhanced glucose uptake resulting into change of a major portion of pyruvate into lactate, even when oxygen is available. This aerobic glycolysis can be referred to as the Warburg effect. Importantly, the tumor microenvironment promotes the migration of malignant glioma cells. In order to investigate if the extracellular lactate could enhance migration of glioma cells via CD44, first the expression of CD44 was analyzed in control and extracellular lactate (40 mM) treated U87 glioma cells by immunocytochemistry.

Figures 2A, 2B, 2C:
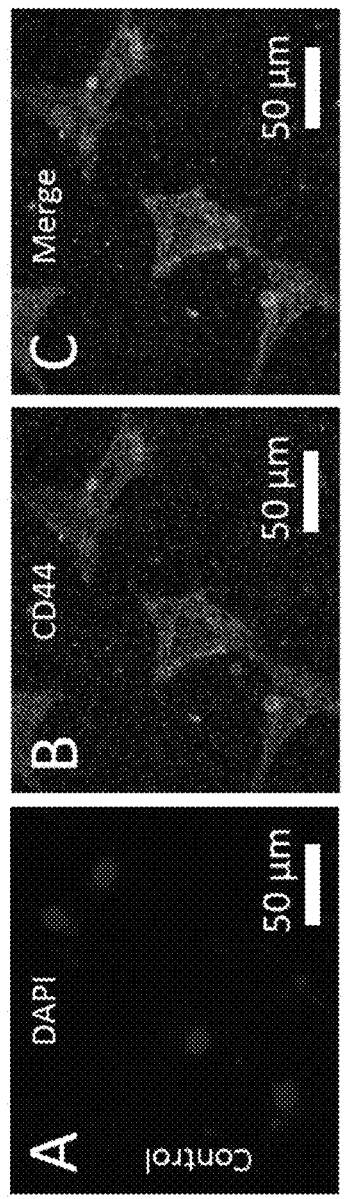
FIG. 2A is an immunofluorescent image (DAPI staining) of CD44 in glioma cells with no treatment (control)
FIG. 2B is an immunofluorescent image of CD44 in glioma cells with no treatment (control)
FIG. 2C is an image formed by merging FIGS. 2A and 2B.
Figures 2D, 2E, 2F:
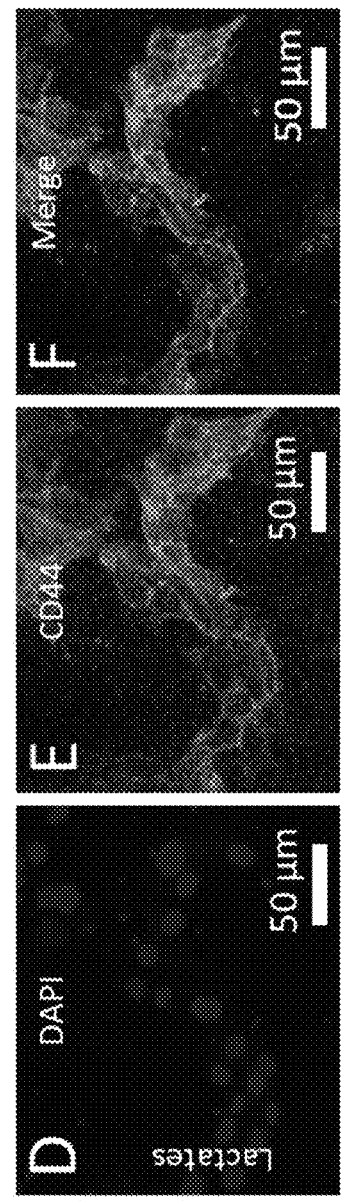
FIG. 2D is an immunofluorescent image of DAPI staining for CD44 in glioma cells with treatment (40 mM lactate treatment for 24 hours)
FIG. 2E is an immunofluorescent image of CD44 in glioma cells with treatment (40 mM lactate treatment for 24 hours)
FIG. 2F is an image formed by merging FIGS. 2D and 2E.
Figure 2M:
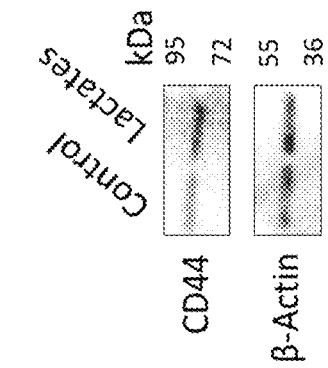
FIG. 2M is a western blot band showing quantification of CD44 in glioma cells with no treatment (control) and with a 40 mM lactate treatment for 24 hours respectively.
Figure 2I:
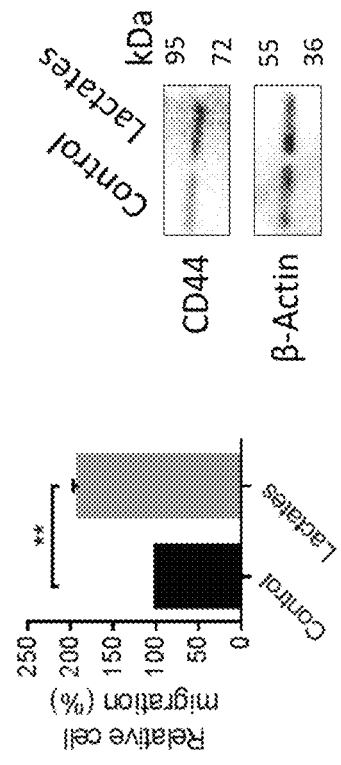
FIG. 2I is a bar graph showing the comparison of relative cell migration (%) between FIGS. 2G and 2H.
Figures 2G, 2H:
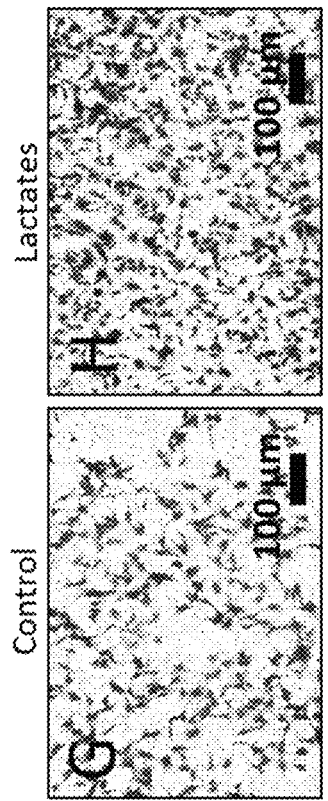
FIG. 2G is an image showing the glioma cells with no treatment (control), as detected by transwell migration assay.
FIG. 2H is an image showing the glioma cells with treatment (40 mM lactate treatment for 24 hours), as detected by transwell migration assay.
Figure 2L:
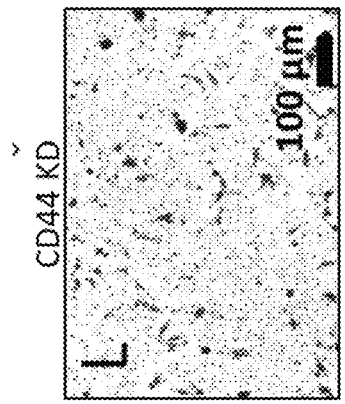
FIG. 2L is an image showing the glioma cells with antisense LNA GapmeR treatment for 24 hours, as detected by transwell migration assay.
Figure 2K:
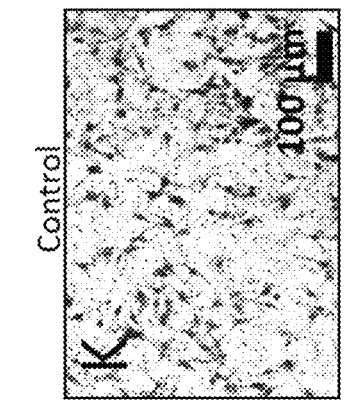
FIG. 2K is an image showing the glioma cells with antisense oligonucleotide control, as detected by transwell migration assay.
Figure 2J:
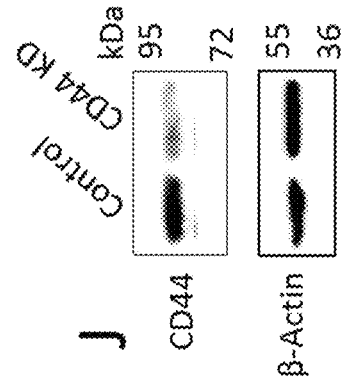
FIG. 2J is a western blot band showing the difference of CD44 in glioma cells with treatment with antisense locked nucleic acid (LNA) GapmeR to CD44 for 24 hours and with treatment with antisense oligonucleotide control respectively.

FIGS. 2A to 2M illustrate that lactate-induced enhanced migration of U87 glioma cells is associated with the upregulation of CD44. FIGS. 2A to 2F show immunofluorescent staining for CD44 in glioma cells with either no treatment (control) (FIGS. 2A to 2C) and with a 40 mM lactate treatment (FIGS. 2D to 2F) for 24 hours. FIGS. 2G to 2I are representative images of glioma cells with enhanced migration by treatment with 40 mM lactate (FIG. 2H) for 24 hours as compared to that of control (FIG. 2G), as detected by transwell migration assay. FIG. 2I us a bar graph showing the comparison of relative cell migration (%) between FIGS. 2G and 2H. FIG. 2J is a western blot band showing the significant knockdown (approximately 90%) of CD44 in glioma cells with treatment with antisense locked nucleic acid (LNA) GapmeR to CD44 for 24 hours as compared to treatment with antisense oligonucleotide control. FIGS. 2K and 2L are representative images of glioma cells with reduced migration by treatment with antisense LNA GapmeR to CD44 for 24 hours as compared to treatment with antisense oligonucleotide control, as detected by transwell migration assay. In the above data are expressed as the mean±SEM. Significance level: ** $P<0.01$, *$P<0.05$, no-treatment control group vs. 40 mM lactate-treated group (FIG. 2I). FIG. 2M shows quantification of CD44 protein in glioma cells with either no treatment (control) or a 40 mM lactate treatment for 24 hours, as determined by western blot analysis. As shown in FIGS. 2A to 2F and 2M, the expression of CD44 is much more significant in cell membrane of U87 glioma cells treated with extracellular lactate as compared to the control group. In addition, the migration of U87 glioma cells was evaluated by transwell migration assay, upon treatment with extracellular lactate for 24 hours. As shown in FIGS. 2G to 2I, extracellular lactate enhanced the migration of glioma cells significantly. Moreover, the KD of CD44 in U87 glioma cells significantly reduced their migration, as seen from FIGS. 2J to 2L. These illustrate that the extracellular lactate promoted glioma cells' migration via CD44.

Extracellular Lactate Enhanced Release of Exosome from Glioma Cells and Exosomal CD44

To investigate the prospective role of exosomal CD44 in the malignant progression of glioma, the characterizations of glioma cells-derived exosomes were performed.

Figures 3A, 3B, 3C:
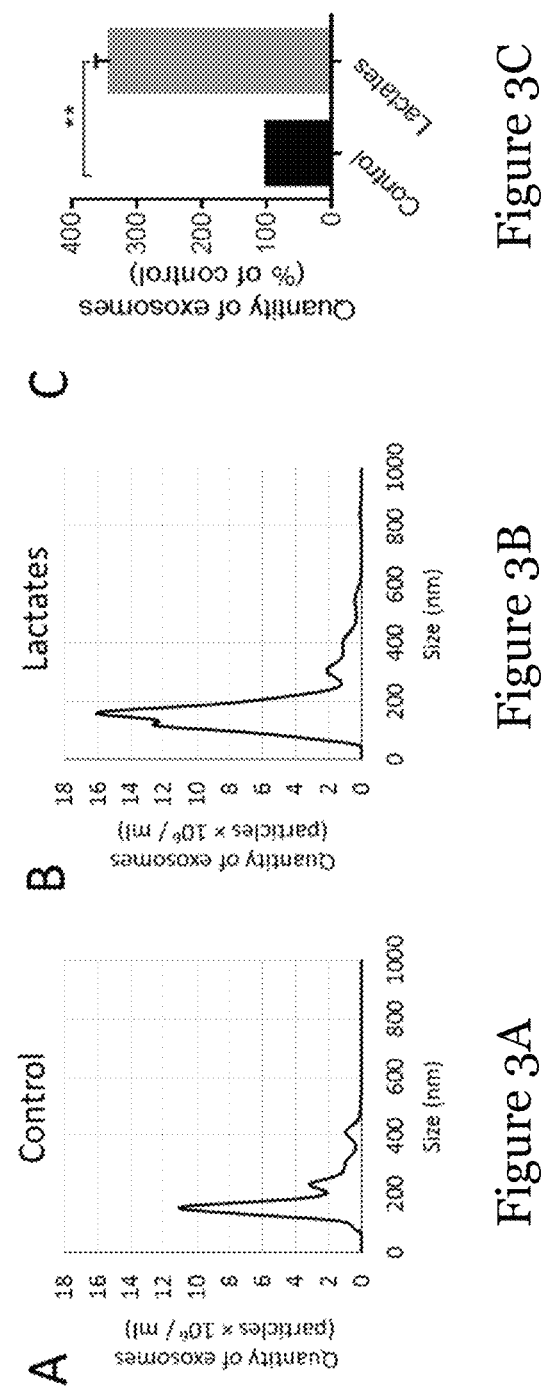
FIG. 3A is a graph showing results of nanoparticle tracking analysis of exosomes released from glioma cells with no treatment (control)
FIG. 3B is a graph showing results of nanoparticle tracking analysis of exosomes released from glioma cells with treatment (40 mM lactate treatment for 24 hours)
FIG. 3C is a bar graph showing the comparison of relative exosomes quantity between FIGS. 3A and 3B.
Figures 3D, 3E, 3F:
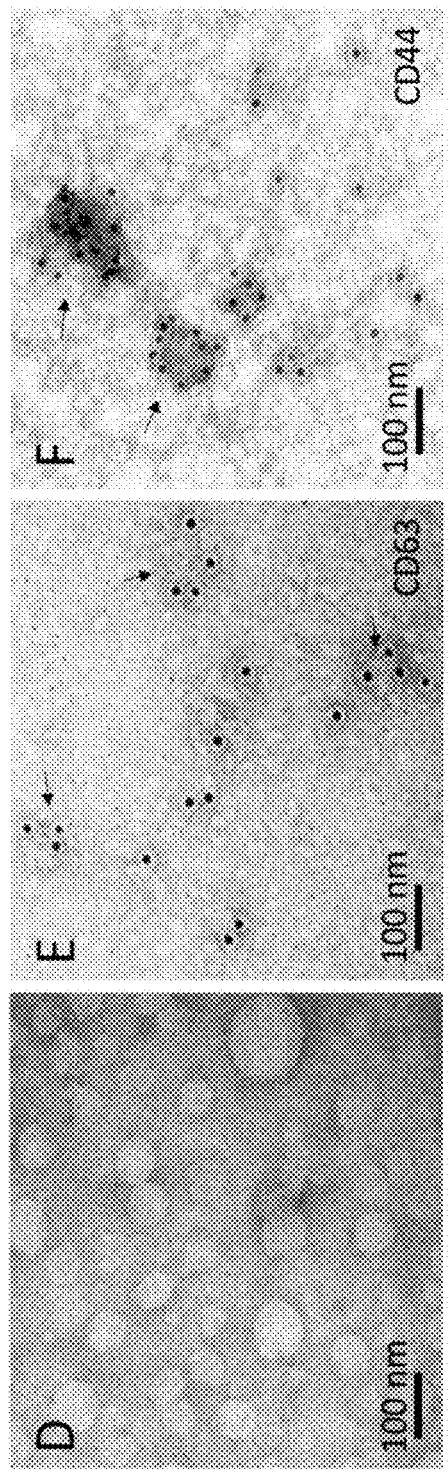
FIG. 3D is a transmission electron microscopy image of exosomes.
FIG. 3E is an immunogold electron microscopy image of CD63 in exosomes isolated from glioma cells.
FIG. 3F is an immunogold electron microscopy image of CD44 in exosomes isolated from glioma cells.
Figure 3G:
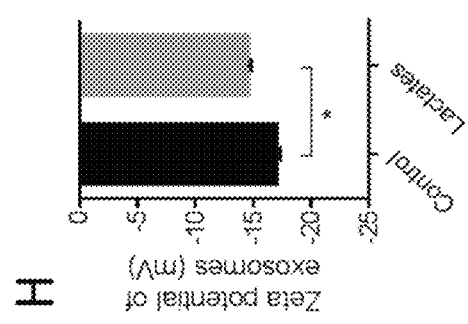
FIG. 3G is a bar graph showing results of ELISA analysis of exosomal CD44 from glioma cells with no treatment (control) and with treatment (40 mM lactate treatment for 24 hours)
Figure 3H:
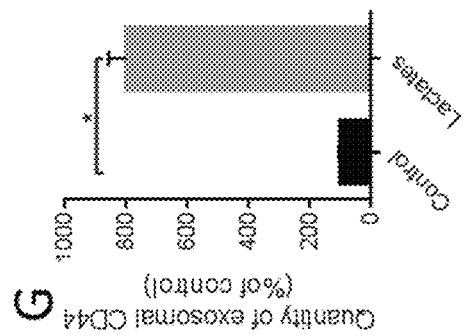
FIG. 3H is a bar graph showing Zeta potential of exosomes released from glioma cells with no treatment (control) and with treatment (40 mM lactate treatment for 24 hours)

To examine whether extracellular lactate could also upsurge the release of exosomes, the amount of exosomes released from U87 glioma cells was analysed by nanoparticle tracking analysis (NTA). FIGS. 3A to 3H illustrate that glioma cells promote the release of CD44-enriched exosomes by treatment with extracellular lactate. FIGS. 3A to 3C show results of nanoparticle tracking analysis of exosomes released from glioma cells with either no treatment (control) (FIG. 3A) and a 40 mM lactate treatment (FIG. 3B) for 24 hours, and a bar graph showing the comparison between FIGS. 3A and 3B (FIG. 3C). Images of transmission electron microscopy for exosomes and immunogold electron microscopy for CD63 and CD44 in exosomes isolated from glioma cells are shown in FIGS. 3D to 3F. FIG. 3G is a bar graph of ELISA result showing the significant increase of exosomal CD44 from glioma cells with treatment of 40 mM lactate for 24 hours as compared to control. FIG. 3H is zeta potential of exosomes released from glioma cells with either no treatment (control) and a 40 mM lactate treatment for 24 hours. In the above data are expressed as the mean±SEM. Significance level: ** $P<0.01$, *$P<0.05$, no treatment control group vs. 40 mM lactate-treated group (FIGS. 3C, 3G, 3H).

As illustrated, the average size of exosome released from control- and 40 mM-extracellular lactate treated U87 glioma cells are 155.5 nm (FIG. 3A) and 160.5 nm (FIG. 3B) respectively. In addition, the release of exosomes was significantly increased in the extracellular lactate treated glioma cells as compared to the control glioma cells (FIGS. 3A to 3C). The morphology and the presence of exosomal marker (here CD63) in the isolated exosomes from U87 glioma cells were analyzed by TEM, and immunogold-EM respectively. The TEM analysis showed heterogeneous size of exosomes; most of them being round shaped along with a few pear shaped exosomes in terms of their morphology (FIG. 3D). The immunogold-EM analysis confirmed the presence of (FIG. 3E) CD63 protein and (FIG. 3F) CD44 protein in the membrane of isolated exosomes from U87 glioma cells. Moreover, extracellular lactate also enhanced the amount of CD44 protein in glioma cells-derived exosomes, as detected by ELISA (FIG. 3G). Furthermore, the zeta potential of the exosomes isolated from lactate-treated glioma cells was enhanced as compared to that obtained from control glioma cells (FIG. 3H). This indicates the role of lactate in tumor microenvironment contributing towards the enhanced release of exosomes from glioma cells, which could be an important marker of malignant glioma progression.

Label-Free Detection of Exosomal Surface Proteins from Glioma Cells by TiN—NH-LSPR Biosensor In order to develop sensitive TIN-NH-LSPR biosensor for detecting exosomal biomarkers, it is crucial to have a sensing chip with the good integrity and strong capacity to capture exosomes. A topographic study for bare- and exosomes captured-TIN-NH-sensing chip was conducted by atomic force microscopy (AFM). The study revealed the great performance of the interaction of TiN—NH-sensing chip with exosomes.

Figures 4A, 4B:
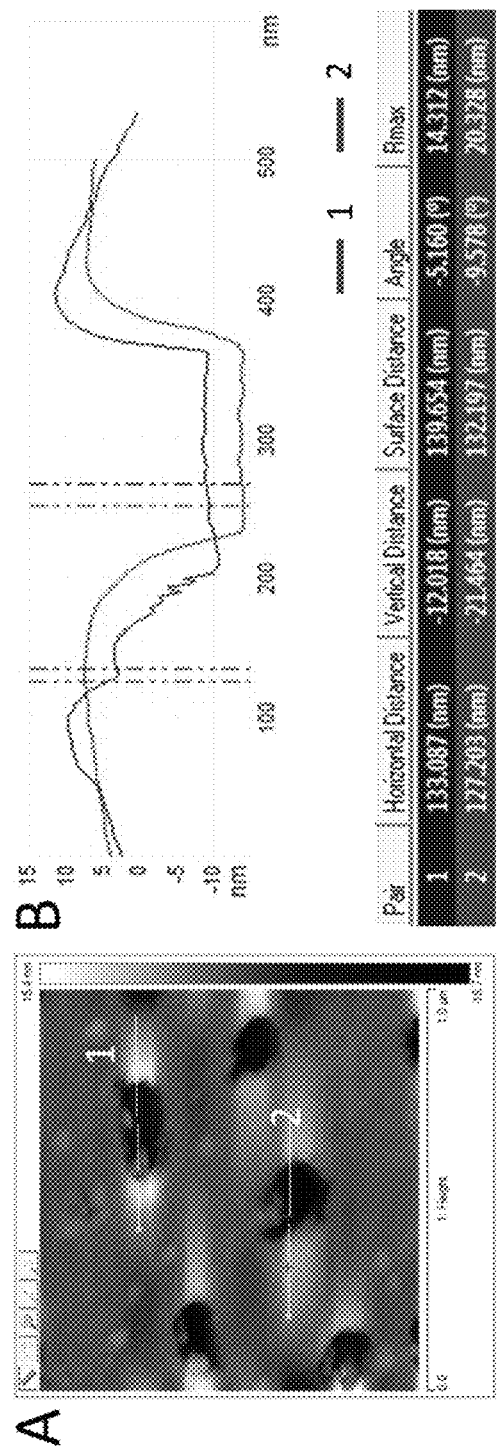
FIG. 4A is a peak force atomic force microscopy topographic image of a TiN—NH chip in 2D (1 μm×1 μm) in one example of the invention.
FIG. 4B is a graph showing the height profile of the surface of TiN—NH chip in the indicated areas 1 and 2 in FIG. 4A.
Figures 6A, 6B:
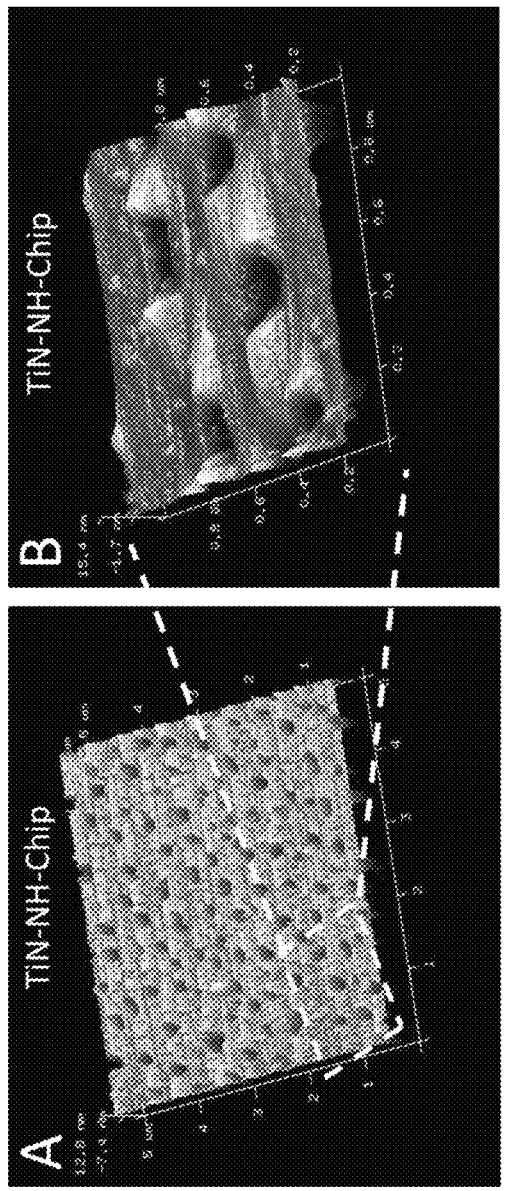
FIG. 6A is a topographic atomic force microscopy image (low resolution) of a TIN-NH chip in one example of the invention.
FIG. 6B is a topographic atomic force microscopy image (high resolution) of a TIN-NH chip in one example of the invention.
Figures 6C, 6D:
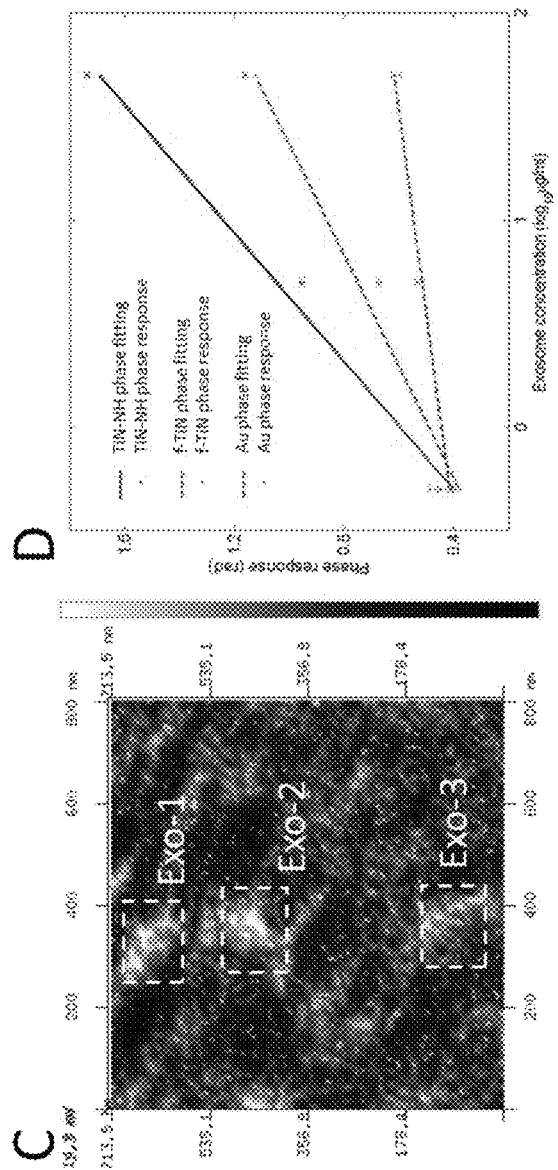
FIG. 6C is a topographic atomic force microscopy image of U87 glioma cells-derived exosomes captured on the surface of TiN—NH chip directly functionalized with biotinylated anti-CD63 antibodies.
FIG. 6D is graph showing the localized surface plasmon resonance phase response of U87 glioma cells-derived exosomes at different concentrations by TiN—NH chip, TiN-film chip, and AuNIs-chip.

FIG. 4A is a peak force atomic force microscopy topographic image of a TiN—NH sensing chip in 2D (1 μm×1 μm) in one example of the invention, and FIG. 4B is a related graph showing the height profile of the surface of TiN—NH chip in the indicated areas 1 and 2 in FIG. 4A. FIGS. 6A and 6B are representative topographic AFM images of bare TiN—NH sensing chip with low resolution (FIG. 6A) and high resolution (FIG. 6B). FIG. 6C is a representative topographic AFM image of U87 glioma cells-derived exosomes captured on the surface of TiN—NH sensing chip directly functionalized with biotinylated anti-CD63 antibodies. FIG. 6D shows the comparison of concentration-dependent SPR phase response of U87 glioma cells-derived exosomes by plasmonic biosensors with TiN—NH-, TiN-film-, and gold-nano-islands-(AuNIs-) sensing chips.

The bare surface of TiN—NH sensing chip was scanned at the scan rate of 1.50 Hz with the scan size of 5 µm by utilizing AFM (FIG. 6A). Furthermore, the high-resolution scanning of TiN—NH sensing chip at the same scan rate with the scan size of 1 µm confirmed that the average diameter of nano-holes was 180.8 nm, and the average distance between two nano-holes was 400 nm (FIGS. 6B, 4A, and 4B).

To detect U87 glioma cells-derived exosomes by TiN—NH-LSPR biosensor, TiN—NH sensing chip was functionalized directly with biotinylated anti-CD63 antibodies. FIGS. 5A to 5D illustrate detection of CD63 in U87 glioma cells-derived exosomes by TIN-NH-LSPR and AuNIs-LSPR biosensors in a concentration-dependent manner. FIGS. 5A and 5B are baseline-LSPR phase responses toward the bare TiN—NH sensing chip functionalized with anti-CD63 antibodies and the chip blocked further with ethanolamine (FIG. 5A), and concentration-dependent LSPR phase response of U87 glioma cells-derived exosomes toward the functionalized TiN—NH chip (FIG. 5B). FIGS. 5C and 5D are baseline phase response of the plasmonic biosensor with the AuNIs sensing chip with treatment with each reagent for its final functionalization with anti-CD63 antibodies (FIG. 5C) and phase response of AuNIs-LSPR biosensor toward U87 glioma cells-derived exosomes in a concentration-dependent manner (FIG. 5D).

In the process of functionalization, the baseline was maintained by flushing PBS for 800 sec, followed by flushing biotinylated anti-CD63 antibodies solution for approximately 2300 sec. Eventually, to block the non-specific sites, ethanolamine solution was flushed until a final phase response was approximately 1.8 rad (FIG. 5A). Various concentrations of U87 glioma cells-derived exosomes were quantitatively detected by the plasmonic biosensor with TiN—NH sensing chip functionalized with biotinylated anti-CD63 antibodies (FIG. 5B) and were compared with that of TiN-film and AuNIs sensing chips. Before the injection of U87 glioma cells-derived exosomes, PBS buffer was allowed to flow across the TIN-NH sensing interface to establish a stable baseline. U87 glioma cells-derived exosomes (0.005-50 µg/ml) were injected into the system independently. A regular increase in the LSPR phase response was observed corresponding to various concentrations of U87 glioma cells-derived exosomes (FIG. 5B). All the samples of U87 glioma cells-derived exosomes were injected via using a peristaltic pump (Reglo Digital, Ismatec) at a flow rate of 30 µl/min. The phase response of TIN-NH-LSPR biosensor was augmented progressively when exosomes were injected into the interface for about 200s and attained the maximum phase value after about 1200s-interaction. Importantly, exosomes concentration-dependent increment of LSPR phase response by the TIN-NH biosensor suggests its auditability for the quantitative detection of exosomes. Subsequently, the sensing chamber of TiN—NH-LSPR biosensor was flushed with PBS to remove non-specific bonded items.

In the comparison of the sensing performance of TiN-film-, TiN—NH- and AuNIs-biosensors, the LSPR sensing performance of AuNIs sensing chip functionalized with anti-CD63 antibodies was directly compared with that of TiN—NH and TiN-film sensing chips. AuNIs-biosensor was functionalized with 11-mercaptoundecanoic acid (11-MUA), and further activated by N-hydroxysuccinimide (NHS), N-(3-dimethylaminopropyl)-N'-ethylcarbodiimide (EDC), as illustrated in FIG. 5C.

In the comparison of sensing characteristics at low concentration range, the phase responses toward exosomes were monitored with TIN-NH, TiN-film and AuNIs sensing chips. The linear sensing calibrations were conducted in the range between 0.005 µg/ml to 5 µg/ml (FIGS. 5D and 6D). The sensitivities were calculated by the regression curve of detecting glioma cells-derived exosomes. The LSPR biosensor with TiN—NH sensing chip exhibited much steeper slope than that of AuNIs sensing chip in the detection-calibration curves of exosomes, indicating that the sensitivity of TiN—NH-LSPR biosensors is better in detecting the glioma cells-derived exosomes. In detecting the glioma cells exosomes of concentrations of 0.05 µg/ml, TiN—NH-LSPR biosensor produced more than twice higher phase response at the equilibrium state than that of AuNIs LSPR biosensor (FIG. 6D).

Non-Invasive Detection of CD44 in Glioma Cells-Derived Exosomes by TiN—NH-LSPR Biosensor to Track Malignant Glioma Progression The increased CD44 expression may be correlated with the enhanced migration of malignant cancer cells, including glioma cells. Also, CD44 was found in glioma cells-derived exosomes. Therefore, CD44 in glioma cells-derived exosomes could be utilized to sense the malignancy of parent glioma cells. In order to determine whether exosomal CD44 can be detected non-invasively for tracking glioma cells' migration with LSPR biosensing, tests and experiments were performed.

Figure 7E:
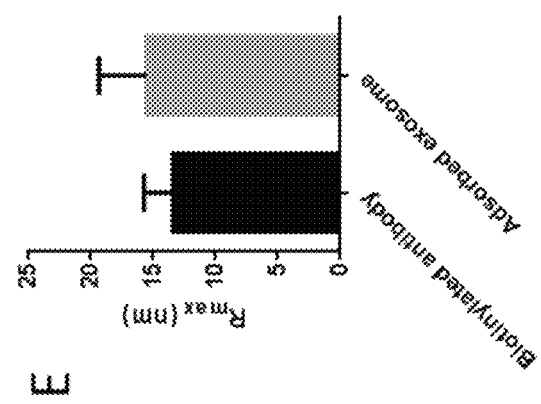
FIG. 7E is a bar graph illustrating the surface roughness of the TIN-NH chip coated with anti-CD44 antibodies and captured U87 glioma cells-derived exosomes by the antibodies on the surface of TiN—NH chip.
Figures 8A, 8B:
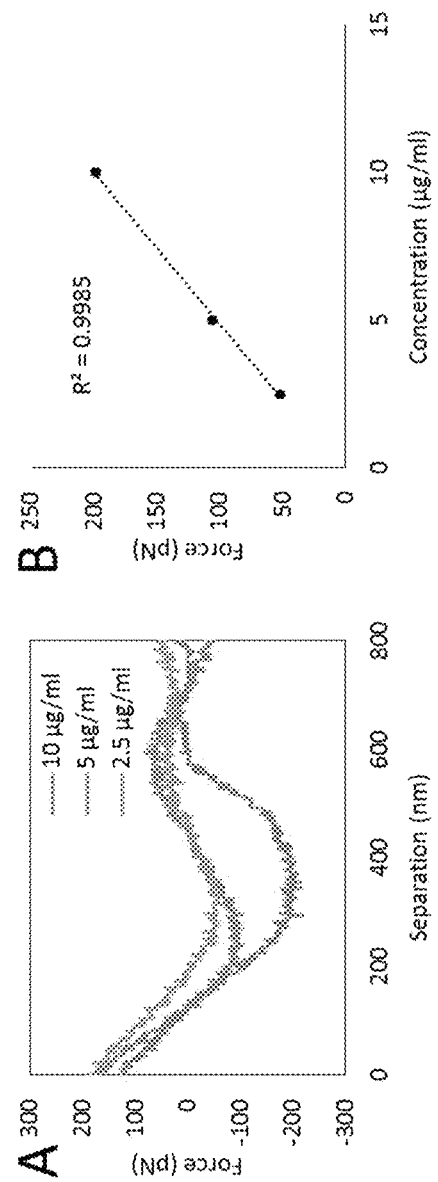
FIG. 8A is a graph showing separation force measurement obtained by atomic force microscopy illustrating differential adhesion force between functionalized anti-CD44 antibodies and CD44 in exosomes from glioma cells for different protein amounts.
FIG. 8B is a graph showing separation force measurement obtained by atomic force microscopy of glioma cells-derived exosomes toward the functionalized atomic force microscopy cantilever tip with anti-CD44 antibodies.
Figures 9A, 9B:
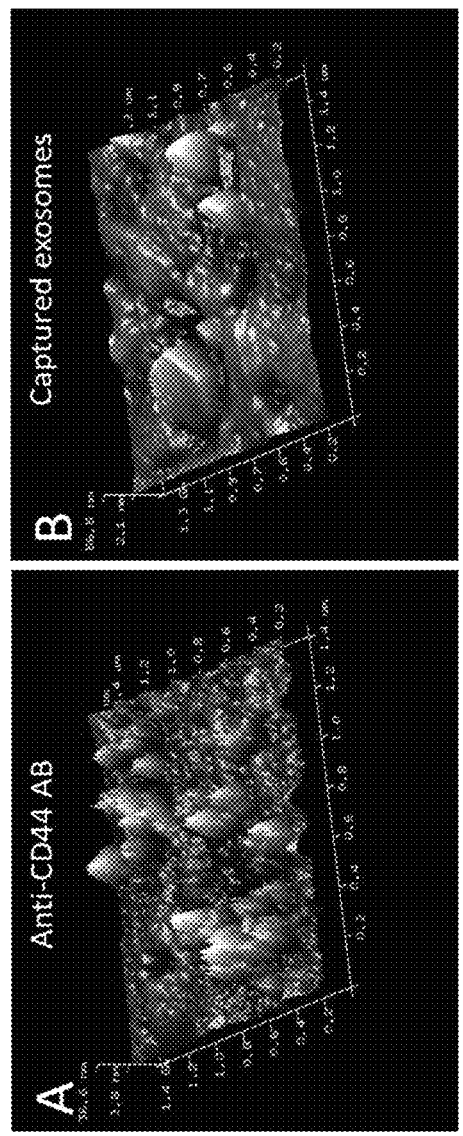
FIG. 9A is an atomic force microscopy scanning image of a TiN—NH chip functionalized with biotinylated anti-CD44 antibodies.
FIG. 9B is an atomic force microscopy scanning image showing glioma cells-derived exosomes captured by the biotinylated anti-CD44 antibodies on the TIN-NH chip of FIG. 9A.

FIGS. 9A to 9E illustrate that TiN—NH-LSPR biosensor can precisely detect enhanced exosomal CD44 by treatment of parent U87 glioma cells with lactate. FIGS. 9A and 9B are AFM scanning image of the TIN-NH sensing chip directly functionalized with biotinylated anti-CD44 antibodies (FIG. 9A), and glioma cells-derived exosomes captured by anti-CD44 antibodies on the TIN-NH sensing chip (FIG. 9B). FIGS. 9C and 9D are concentration-dependent LSPR phase response of glioma cells-derived exosomes toward the functionalized TiN—NH sensing chip with anti-CD44 antibodies (FIG. 9C), and the corresponding calibration curve revealing the strong correlation between LSPR phase response and exosome quantity (FIG. 9D). FIG. 9E shows the LSPR phase response of minimum quantity of exosomes from U87 glioma cells with (experimental group) and without (control group) lactate treatment toward the functionalized TiN—NH sensing chip with anti-CD44 antibodies. FIGS. 7A to 7D show the rulesets of topographic analysis of the TIN-NH sensing chip functionalized with anti-CD44 antibodies and captured exosomes by the antibodies on the surface of chip. Peak force AFM topographic image with two dimensions (2.1 µm×2.1 µm) and height profile of the surface of TiN—NH chip coated with anti-CD44 antibodies are shown in FIGS. 7A and 7B. Peak force AFM topographic image with two dimension (2.1 µm×2.1 µm) and height profile of the surface of TiN—NH chip coated with anti-CD44 antibodies and captured U87 glioma cells-derived exosomes by the antibodies on the surface of TiN—NH chip are shown in FIGS. 7C and 7D. FIG. 7E is a bar graph representing roughness of the surface of TiN—NH chip coated with anti-CD44 antibodies and captured U87 glioma cells-derived exosomes by the antibodies on the surface of TiN—NH chip. FIGS. 8A and 8B show the detection of CD44 in glioma cells-derived exosomes by TIC-AFM. FIG. 8A illustrates separation force curves by TIC-AFM revealing the differential adhesion force between anti-CD44 antibodies and CD44 in exosomes (2.5, 5, and 10 µg/ml of protein amount) from glioma cells. FIG. 8B shows the concentration-dependent TIC-AFM response of glioma cells-derived exosomes toward the functionalized AFM tip with anti-CD44 antibodies.

As shown in FIG. 9A, biotinylated anti-CD44 antibodies-functionalized TiN—NH chip was utilized. Exosomes captured on the chip was also characterized by the AFM scanning. The exosomes were captured on biotinylated anti-CD44 antibodies directly absorbed on the surface of TiN—NH chip through exosomal CD44 antigen, and visualized with AFM (FIG. 9B). Moreover, the AFM scanning of biotinylated anti-CD44 antibodies-functionalized TiN—NH chip showed the average height of 26.66 nm and the roughness (Rmax) of 13.39 nm (FIGS. 9A, 7A, 7B, and 7E). Subsequently, U87 glioma cells-derived exosomes were captured on the surface of TiN—NH chip, and their scanning profile of AFM images showed the average height of 51.66 nm and the Rmax of 15.55 nm, indicating that the U87 glioma cells-derived exosomes were captured in the space between two consecutive nano-holes (FIG. 9B, 7C to 7E). Furthermore, to detect exosomal CD44, various concentrations of exosomes derived from U87 glioma cells, i.e., 0.005 µg/ml to 500 µg/ml, were utilized. The detection of exosomal CD44 by TiN—NH-LSPR biosensor was carried out using anti-CD44 antibodies coated chip with over the range from 0.005 µg/ml to 50 µg/ml of exosome concentrations (FIG. 9C). The linear regression equation is: $y=1.447 \times x + 0.027$ (with R-square 0.997) (FIG. 9D). Based on the IUPAC definition, the limit of detection (LOD) with the LSPR biosensor with the anti-CD44 antibodies-functionalized TiN—NH chip was $3.46 \times 10^{-3}$ µg/ml, indicating its high sensitivity in detecting exosomal CD44 (FIGS. 8A and 8B).

After establishing the sensitivity range and LOD of TiN—NH-LSPR biosensor for the detection of exosomal CD44, the equal amount of exosomes derived from control- and 40 mM lactate treated-U87 glioma cells, were tested by the LSPR biosensor with the anti-CD44 antibodies functionalized TiN—NH chip. The LSPR phase response for the exosomes derived from lactate treated U87 glioma cells was found to be significantly higher as compared to that of the exosomes derived from control group (FIG. 9E), which was correlated with the enhanced cell migration of parent U87 glioma cells. Therefore, it is shown that the detection of exosomal CD44 by TiN—NH-LSPR biosensor can be utilized to sense the migration ability of glioma cells, implying its usefulness in the glioma liquid biopsy.

Non-Invasive Detection of Interaction Between Exosomal CD44 and Hyaluronic Acid by TiN—NH-LSPR Biosensor to Determine Malignant Glioma Progression Since CD44 is a receptor for hyaluronic acid, which plays a role in enhancing the migration of glioma cells by their interaction, AFM force-separation analysis was conducted to determine and distinguish level of CD44 in the control- or lactate treated-U87 glioma cells-derived exosomes captured on the surface of TiN—NH chip through anti-CD63 antibodies via using anti-CD44 antibodies- or hyaluronic acid-functionalized-AFM tip. The exosomes immobilized on the TIN-NH chip was scanned by AFM and was further confirmed by the analysis of their size (FIGS. 9A and 9B), followed by the AFM force-separation analysis.

FIGS. 10A to 10C illustrate that the TIC-AFM biosensor captures exosomes and detects exosomal CD44 consecutively as a single molecule force spectroscopy. FIG. 10A is a schematic representation of TIC-AFM biosensor for the specific capture of exosomes by anti-CD63 antibodies absorbed on the TiN—NH discs and the consecutive detection of exosomal CD44 by anti-CD44 antibodies, or hyaluronic acid, a natural ligand, functionalized in the cantilever sensing tip. FIG. 10B shows separation force curves by TIC-AFM revealing the differential adhesion force between anti-CD44 antibodies, or hyaluronic acid, and CD44 in exosomes from glioma cells with (experimental group) and without (control group) treatment of lactate. FIG. 10C is the corresponding bar graph showing the comparison of adhesion force between groups. All data are shown as the mean±SEM. Significance level: ** $P<0.01$, * $P<0.05$, condition 1 vs condition 2; condition 3 vs condition 4 (FIGS. 10B and 10C).

FIG. 10A shows two sensors 200A, 200B, each operable for use in atomic force microscopy associated with exosomal CD44 detection. Sensor 200A includes a titanium nitride nano-holes (TIN-NH) chip 202A with a surface functionalized with biotinylated anti-CD63 antibodies. The surface (and optionally the entire chip 202A) can be made with titanium nitride or titanium nitride-based material. The biotinylated anti-CD63 antibodies are arranged to engage with CD63 on the surface of exosomes associated with the glioma cells. The sensor 200A also includes cantilever 204A for atomic force microscopy and arranged to operably cooperate with the chip 202A. The cantilever 204A has a tip with a tip surface functionalized with biotinylated anti-CD44 antibodies, arranged to engage with CD44 on the surface of exosomes associated with the glioma cells, for atomic force microscopy force-separation analysis. Sensor 200B is similar to sensor 200A, except that the cantilever 204B has a tip with a tip surface functionalized with biotinylated hyaluronic acid, arranged to engage with CD44 on the surface of exosomes associated with the glioma cells, for atomic force microscopy force-separation analysis. The sensors 200A and 200B can capture exosomes and can be used in atomic force microscopy, to determine differential adhesion force between anti-CD44 antibodies on the tip and CD44 in U87 glioma cells-derived exosomes, which indirectly reflect the progression of glioma.

The AFM force-separation analysis showed the capability of detection of the interaction between exosomal CD44 and anti-CD44 antibodies- or hyaluronic acid, although it revealed a significantly higher separation force for hyaluronic acid-functionalized AFM tip toward control exosomes, as compared with anti-CD44 antibodies-functionalized AFM tip. This indicates a strong interaction between exosomal CD44 and hyaluronic acid (force curves 1 and 2 in FIG. 10B). In addition, the force was further enhanced when lactate-treated U87 glioma cells-derived exosomes were used, indicating a correlated increase in force when lactate driven exosomal CD44 was enhanced (force curves 3 and 4 in FIG. 10B). The corresponding bar graph representing the average AFM force response in the various conditions (as depicted in FIG. 10B) is shown FIG. 10C.

Non-Invasive Detection of CD44 in EGFRvIII-Specific U87 Glioma Cells-Derived Exosomes in Mouse Blood Serum EGFRVIII mutant proteins have been found to be associated with various aggressive progression of cancer cells, such as invasion and angiogenesis in glioma cells. Also, their increased expression may be associated with the poor prognosis of glioma. In one embodiment, exosomal EGFRVIII mutant protein can be utilized as a great biomarker to diagnose and prognoses glioma as well as it can be used to capture glioma-derived exosomes. In order to identify the glioma cells-derived exosomes, the presence of EGFRVIII was analyzed in control exosomes (isolated from HEK cells) and U87 glioma cells-derived exosomes by immunogold EM technique.

Figures 11A, 11B, 11C:
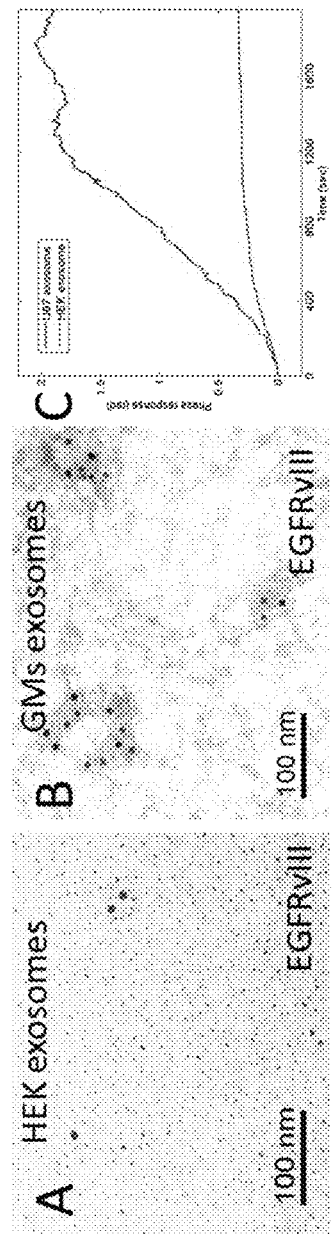
FIG. 11A is an immunogold electron microscopy image of EGFRVIII in HEK-derived exosomes.
FIG. 11B is an immunogold electron microscopy image of EGFRVIII in U87 glioma cells-derived exosomes.
FIG. 11C is a graph showing the localized surface plasmon resonance phase response with TiN—NH chip functionalized with anti-EGFRvIII antibodies toward U87 glioma cells-derived exosomes.
Figures 11D, 11E:
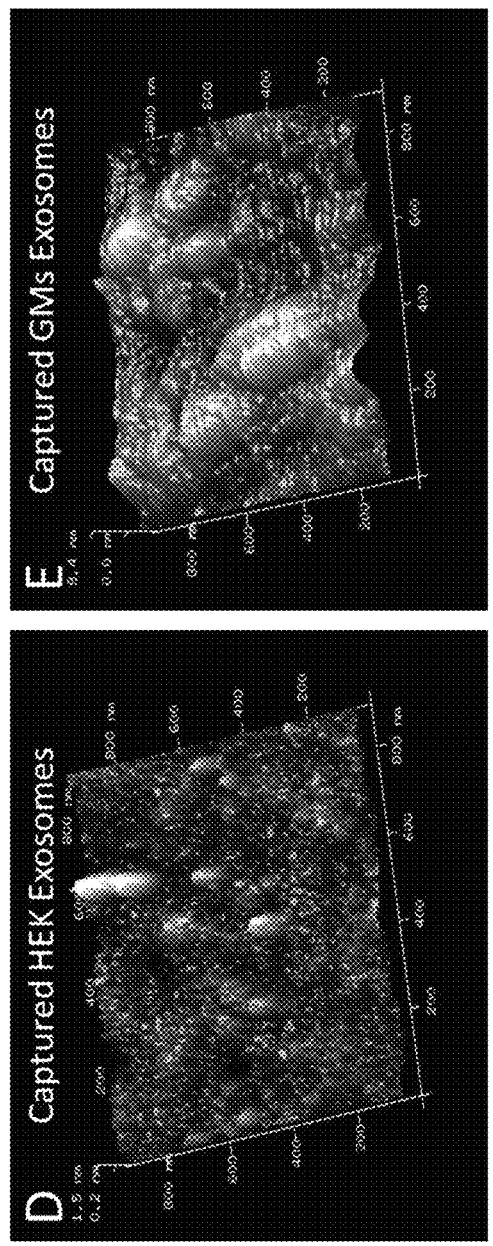
FIG. 11D is a topographic atomic force microscopy image the HEK-derived exosomes captured by anti-EGFRVIII antibodies on the TIN-NH discs.
FIG. 11E is a topographic atomic force microscopy image of the U87 glioma cells-derived exosomes captured by anti-EGFRVIII antibodies on the TIN-NH discs.

FIGS. 11A to 11I illustrate that the TIC-AFM biosensor detects CD44 in glioma cells-derived exosomes captured by anti-EGFRVIII antibodies on the TiN—NH discs. FIGS. 11A and 11B are Immunogold-EM images of EGFRVIII in HEK-derived exosomes (negative control) (FIG. 11A) and U87 glioma cells-derived exosomes (FIG. 11B). FIG. 11C shows the phase response of the LSPR plasmonic biosensor with TiN—NH sensing chip functionalized with anti-EGFRVIII antibodies toward U87 glioma cells-derived exosomes. FIGS. 11D and 11E are AFM topographic images of captured HEK-derived exosomes (FIG. 11D) and U87 glioma cells-derived exosomes (FIG. 11E) by anti-EGFRVIII antibodies on the TiN—NH discs. FIGS. 11F and 11G are AFM force curves showing the differential adhesion force between anti-CD44 antibodies on the tip and CD44 in U87 glioma cells-derived exosomes captured by anti-EGFRVIII antibodies on the TiN—NH discs as compared to that of control (FIG. 11F) and the corresponding bar graph summarizing their relative strength (FIG. 11G). FIGS. 11H and 11I are AFM force curves showing the differential adhesion force between anti-CD44 antibodies on the tip and CD44 in glioma cells-derived exosomes captured by anti-EGFRVIII antibodies from their mixture with serum-derive exosomes as compared to that of control (FIG. 11H) and the corresponding bar graph summarizing their relative strength (FIG. 11I). All data are shown as the mean±SEM. Significance level: ** $P<0.01$, experimental group vs. control group.

As shown in the Figures, a significantly high number of EGFRvIII-labelled gold particles were found in U87 glioma cells-derived exosomes as compared to that in HEK exosomes (FIGS. 11A and 11B). Nevertheless, the anti-EGFRVIII antibodies used in this experiment might not be completely specific because some of human embryonic kidney (HEK) cells-derived exosomes also revealed some of very weak positive labeling (FIG. 11A).

Furthermore, glioma-specific exosomal EGFRVIII was detected by LSPR biosensor with TiN—NH-chip-functionalized with anti-EGFRVIII antibodies. The TiN—NH-LSPR biosensor revealed its good selectivity for exosomal EGFRVIII in the phase response towards glioma cells-derived exosomes as compared control HEK cells-derived exosomes. The phase response was found to be 0.23 and 1.73 radian for exosomes isolated from HEK cells and glioma cells, respectively. As expected from the data of immunogold EM, HEK cell-derived exosomes also produced weak phase response, presumably caused by the non-specific interaction between anti-EGFRVIII antibody and some of exosomal antigens, such as a wild type of EGFR. These non-specific bindings were partially removed by PBS flushing and obvious dissociation occurred (FIG. 11C). Since, EGFRVIII may be considered as a glioma specific membrane mutant protein, it could be utilized to capture the glioma specific exosomes. To accomplish this TiN—NH chip was directly functionalized with biotinylated anti-EGFRVIII antibody, followed by immobilization of glioma cells-derived exosomes and HEK exosomes. Importantly, a significant number of U87 glioma cells-derived exosomes were captured by anti-EGFRVIII antibody as compared to that of HEK (FIGS. 11D to 11E). This demonstrated that U87 glioma cells-derived exosomes were EGFRVIII positive as compared to that derived from HEK, which was acting as a negative control. Furthermore, to detect level of CD44 on the membrane of EGFRVIII-positive exosomes from U87 glioma cells, potentially in in vivo as liquid biopsy; U87 glioma cells-derived exosomes were mixed with mouse blood serum, mimicking in vivo environment. It was found that AFM force towards CD44 in U87 glioma cells-derived exosomes when mixed with mouse blood serum was significantly larger as compared to that in only mouse blood serum-derived exosomes (control group) (FIGS. 11F to 11I). This demonstrated that exosomal CD44 could be utilized a prospective biomarker for determining the capacity of parent glioma cells migration, together with capturing glioma cells-derived EGFRVIII-positive exosomes.

Exosomes from Glioma Cells, Stimulated by Extracellular Lactate, Increase the Tube Formation of ECs as Well as the Migration of Glioma Cells with a CD44-Dependent Manner To understand the role of glioma cells-derived exosomes as functional mediators through CD44 in the migration of glioma cells and tube formation of ECs, exosomes were first isolated from control- or lactate-treated glioma cells, and were further incubated with glioma cells for 24 hours.

FIGS. 12A to 12L illustrate increased CD44 in glioma cells by lactate promotes glioma progression partly via exosomes. Autologous (FIGS. 12A to 12C) and heterologous (FIGS. 12D to 12F) uptake of exosomes from the glioma cells with (FIGS. 12B, 12E) and without (FIGS. 12A, 12D) treatment of 40 mM lactate and with treatment of CD44-antisense LNA GapmeR oligonucleotides (FIGS. 12C, 12F), into glioma cells or ECs (Blue: DAPI, Red: Phalloidin, Green: Exo-Green). Effect of autologous (FIGS. 12G to 12I) and heterologous (FIGS. 12J to 12L) uptake of each group of exosomes into glioma cells' migration, or ECs' tube formation, respectively.

As shown in these Figures, enhanced migration of glioma cells was clearly observed, when incubated with lactate treated glioma cells-derived exosomes as compared to control glioma cells-derived exosomes (FIG. 12A, 12B, 12G, 12H). Similarly, enhanced number of tubes were formed in ECs (seeded as monolayer on the Geltrex), when incubated with lactate treated glioma cells-derived exosomes as compared to the control glioma cells-derived exosomes (FIG. 12D, 12E, 12J, 12K). Furthermore, to investigate the effect of change of exosomal CD44 level in migration of glioma cells or tube formation of ECs, CD44-reduced exosomes were produced by the transfection of CD44 antisense oligonucleotides in parent glioma cells. The effect of reduced exosomal CD44 on the migration of glioma cells and tube formation of ECs were investigated. It was found that reduced exosomal CD44 significantly decreased glioma cells' migration (FIGS. 12 C and 12I) and decreased the tube formation in ECs by their treatment with each cell type (FIGS. 12F and 12L). This demonstrated the potential role of glioma cells-derived exosomal CD44 in tube formation of ECs and migration of glioma cells directly or indirectly, leading to tumor progression.

Miscellaneous

1. Cell Culture

The human U87 glioma cells and bEnd.3 endothelial cells (ECs) in the above examples/experiments were cultured and maintained in Dulbecco's modified essential medium (DMEM) (Life Technologies) with high glucose supplemented with 10% fetal bovine serum (FBS), and 1% penicillin-streptomycin at 37° C. with 5% CO2 in a humidified incubator. Glioma cells were grown to around 70% confluency, washed 3 times with phosphate buffered saline (PBS), and incubated with serum-free media for 24 hours for isolation of exosome.

2. Treatment of Glioma Cells with Lactate

In the above examples/experiments, glioma cells with around 70% confluency were treated with vehicle (control) and 40 mM solution of sodium-L-lactate (Sigma) for 24 hours.

3. Cell Migration Assay

In the above examples/experiments, Transwell migration assay was used as an in-vitro model for standard cell migration. 24-well Transwell Permeable Support chambers (Costar, Cat #3422) with a pore size of 8.0 μm were used. 100 μl of glioma cells suspension (1×106/ml) and 500 μl of complete medium were added to the upper- and the lower-chamber, respectively. The medium was removed after 24 hours-culture at 37° C. with 5% CO2 in the humidified incubator. Next, glioma cells on the plates were fixed for 10 minutes with 4% paraformaldehyde (PFA), then the plates were inverted, and the fixed glioma cells were air-dried. The glioma cells were stained in 0.1% crystal violet solution for 20 minutes and washed 3 times with PBS. The wells were gently wiped with a swab. At least, 6 pictures were taken randomly from different locations via using an inverted microscope at 10× magnification. Number of migrated cells was counted via using ImageJ software.

4. Immunocytochemistry

In the above examples/experiments, glioma cells were cultured on poly-D-lysine (Merck, Cat #A-003-E)-coated coverslips (Marien-field-superior) until 60-70% confluence, followed by treatment with 40 mM solution of lactate for 24 hours. Then, the cells were fixed with 4% paraformaldehyde (PFA) in phosphate buffer saline (PBS) for 1 hour on ice. After washing the cells with PBS containing 0.05% Triton X-100 (PBST) 3 times for 10 minutes, the fixed cells were treated with the blocking solution containing 5% bovine serum albumin (BSA) in PBST, for 1 hour. Next, the cells were incubated overnight at 4° C. with anti-CD44 primary antibodies in 0.1% BSA in PBST (rabbit anti-CD44 antibodies=1:200 dilution; Cat #ab189524). After washing 3 times with PBST for 10 minutes, the cells were incubated with secondary antibodies (goat anti-rabbit Alexa Fluor 488, dilution at 1:500 with 0.1% BSA in PBST) for 2 hours at room temperature in a dark humidified chamber. After washing with PBST 3 times for 10 minutes, the stained cells on the coverslips were mounted with a drop of Vectashield with DAPI (Vector Laboratories, Cat #H-1200) onto glass slides. Images were captured with a Zeiss Laser Scanning Microscope LSM 880 NLO with Airyscan.

5. Isolation of Exosomes

In the above examples/experiments, exosomes from glioma cells were isolated using Total Exosome Isolation (TEI) kit (Cat #4478359) as per the standard protocol. In brief, the FBS-free conditioned medium from cultured glioma cells was first harvested and centrifuged at 2000×g for 30 minutes to remove cells and debris. The supernatant containing cell-free culture media was transferred to a new tube without disturbing the pellet. Then, a half volume of the TEI reagent was added to the supernatant, followed by mixing the culture media/reagent until the solution becomes homogenous. Then, the mixed samples were incubated at 2° C. to 8° C. overnight. After incubation, the samples were centrifuged at 10,000×g for 1 hour at 2° C. to 8° C. After the supernatant was discarded, the resultant exosomes pellet at the bottom of the tube was re-suspended in 1×PBS. The isolated exosomes were quantified based on the protein amount which was determined by Pierce BCA Protein Assay Kit (Thermo Fisher Scientific).

For immunogold labeling, purified exosomes suspended in PBS were placed on formvar carbon coated nickel grids, blocked, and incubated 6. Characterization of Glioma Cells-Derived Exosomes In the above examples/experiments, the morphology and particle size of exosomes were characterized via using transmission electron microscopy (TEM). The size distribution and the concentration of exosomes were further analyzed with nanoparticle tracking analysis (NTA) via using Malvern NanoSight NS300. For the detection of CD63, EGFRVIII, and CD44 in exosomes, immunogold-EM analysis was performed. Briefly, for immunogold labeling, exosomes in PBS were fixed with 4% PFA. The fixed exosomes were placed on Formvar-carbon coated EM grid and blocked with PBS/5% BSA solution for 10 minutes. Then, fixed exosomes in blocked grids were transferred to a drop of anti-CD63 (Abcam, Cat #ab68418)- or anti-EGFRVIII (Bioss, Cat #bs-2558R)- or anti-CD44 (Abcam, Cat #ab189524)-primary antibodies (dilution=1:100) solution in PBS/0.5% BSA, and incubated for 1 hour. After washing with PBS 3 times for 10 minutes, the exosomes in the grids were further incubated with goat anti-rabbit IgG H&L (10 nm gold) pre-adsorbed (Abcam, Cat #ab27234) secondary antibodies solution in PBS/0.5% BSA for 30 minutes, and then washed 3 times for 10 minutes with 100 μl PBS. The exosomes in the grids were stained with 2% uranyl acetates, and then viewed under transmission electron microscope (FEI/Philips Tecnai 12 BioTWIN).

7. Biotinylation of Anti-CD63, Anti-EGFRVIII, and Anti-CD44 Antibodies

N-hydroxysuccinimide activated biotin (NHS-biotin) reacts with the primary amine groups of antibodies in the biotinylation of antibodies. Therefore, in the above examples/experiments, to produce biotinylated anti-CD63, anti-EGFRVIII, or anti-CD44, first, the NHS-biotin solution was prepared in a concentration of 40 mg/ml in dry DMSO. Then, 3 mL antibodies in PBS (0.5 mg/ml concentration at pH 7.4) are mixed with 6 μL stock NHS-biotin solution while stirring at room temperature for 2 hours in the dark. Finally, the biotinylated antibodies solution was added 6 μL of 0.5 M ethanolamine and incubated for 30 minutes. The prepared solution was purified several times with small disposable columns to remove the free biotin.

8. Synthesis of SAM-AuNIs Sensing Chip and Functionalization with Antibodies for Detection of Glioma Cells-Derived Exosomes The synthesis of SAM-AuNIs sensing chip was performed in the above examples/experiments. Briefly, the SAM-AuNIs sensing chip was synthesized by annealing the as-deposited Au films (thickness around 5.0 nm, surface roughness of 0.79 nm) on a BK7 glass slide, followed by thermal annealing at 550° C. for 3 hours in air.

The functionalization of SAM-AuNIs sensing chip with anti-CD63 antibodies was performed. Briefly, the dry BK7 slide with SAM-AuNIs were cleaned with absolute ethanol, followed by incubation of SAM-AuNIs in MUA solution (10 mM) for 30 minutes. The MUA carboxyl functional group was activated by adding freshly prepared 2-(N-Morpholino) ethane sulfonic acid (MES) solution for 20 minutes. Then, 2 μg/ml anti-CD63 antibodies in PBS buffer was immobilized on the AuNIs for 40 minutes, followed by removal of excessive antibodies by rinsing with PBS buffer, and unbound sites were blocked by 1M of ethanolamine. Eventually, exosomes solutions were injected sequentially over the antibody-functionalized surface.

9. Synthesis of TiN-Film- and TiN—NH-Chips and Functionalization with Biotinylated Antibodies for Detection of Glioma Cells-Derived Exosomes The synthesis of TiN-film-sensing chip was performed by direct deposition approach with radio-frequency magnetron sputtering. Briefly, the BK7 glass slides were initially mounted on the rotating fixture and evacuated to a base pressure of 10-7 Torr. During the magnetron sputtering with TiN target at 100 W radio-frequency power, the vacuum was at 6×10-3 Torr and the Ar flow was kept at 20 sccm. The film thickness was controlled by monitoring the sputtering time duration.

Figure 13:
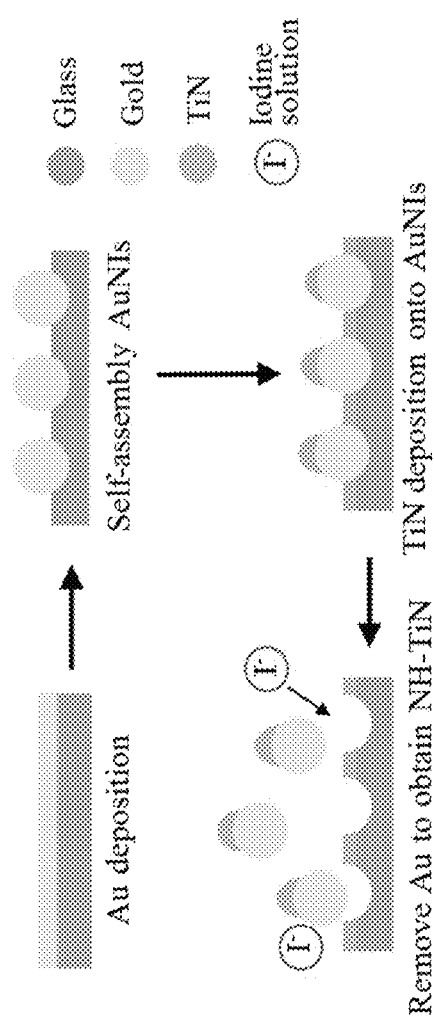
FIG. 13 is a schematic diagram of a method for making a sensor for liquid biopsy in one embodiment of the invention.

TIN-NH-chips were synthesized with sacrificed AuNIs method as shown in FIG. 13. In detail, Gold (Au) thin film was deposited on the glass substrate, followed by 9 hours annealing at 550° C. Then, the Au will gather together to form AuNIs and these islands will sink into the substrate at their respective positions when the glass becomes soft under the elevated temperature. Afterwards, an ultrathin TiN thin film will deposit on top of AuNIs and the AuNIs will not be totally covered by TiN. Thus, the AuNIs could be chemically removed by immersing the sensor chips in AN-50, a gold-dissolved solution. In this way, TiN—NH-sensing chip was synthesized. Then, the biotinylated anti-CD63 or anti-CD44 antibodies could directly or indirectly attach to the surface of the TiN—NH-sensing chips.

Figure 14:
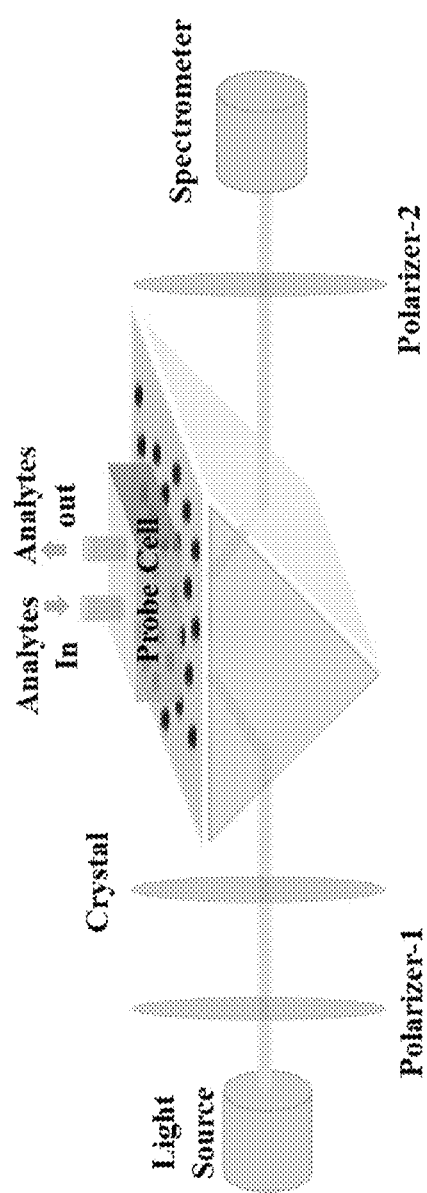
FIG. 14 is a schematic diagram of a method for using a sensor for liquid biopsy in one embodiment of the invention.

FIG. 14 shows the TIN-NH-sensing chip used in LSPR bio-sensing for glioma liquid biopsy. The common-path white light interferometric system and differential phase modulating method were used to perform the label-free detection of glioma cells-derived exosomes with the TiN-film and TIN-NH-LSPR biosensors. Briefly, PBS buffer was initially injected into the sensing chamber to build the detection baseline for at least 200s. Then the glioma cells-derived exosomes were injected into the sensing chamber with constant flow rate at 30 µl/min. Then the biosensing interface was flushed with PBS subsequently to remove the non-specific bonded items. The differential phase response was retrieved by using windowed Fourier transform (WFT) method in real-time scheme. The sensitivity of TiN—NH LSPR biosensor for the detection of exosomal CD63, an exosome marker, was compared with that of SAM-AuNIs-, and TiN-film biosensors via measuring phase responses with an exosome quantity-dependent manner.

10. Sensing Glioma Cells-Derived Exosomal CD44 by TIC-AFM Biosensor.

In order to study the interaction of hyaluronic acid with CD44- or to detect CD44-on glioma cells-derived exosomes, the exosomes were firstly immunocaptured on the TIN-NH discs via the functionalization of biotinylated anti-CD63 antibodies. The AFM tip (ScanAsyst-Fluid, TELTEC semiconductor pacific limited) was functionalized with anti-CD44 antibodies. Briefly, anti-CD44 antibodies (dilution 1:200) were covalently attached to Si3N4 AFM probes via thiol ester linkage (Bruker), followed by washing of probes in PBS, blocking with 1% BSA-PBS for 1 h, and eventually rinsing with PBS.

AFM tip was functionalized with hyaluronic acid. Briefly, the AFM cantilevers were conditioned by exposure to UV for 30 min, and then immersed overnight at 4° C. in an ethanolic solution of OEG disulfide and b-OEG thiol (molar ratio 500:1) at a total concentration of 1 mM. Prior to use, the functionalized substrates were rinsed with ethanol and blow-dried with N2. This procedure provides a monolayer of oligo(ethylene glycol) (OEG) that is inert to non-specific binding of proteins and glycosaminoglycans (GAGs); it permits the formation of a monolayer of streptavidin that serves as a "molecular breadboard" for the controlled anchorage of biotin-tagged molecules. For anchorage of hyaluronic acid, the surfaces were incubated with biotinylated-hyaluronic acid at the concentration of 2 µg/ml. The silicon nitride cantilevers used in the study were calibrated to determine the spring constants to be 0.06420 N/m. The adhesion force between functionalized AFM tips and captured exosomes were recorded with single ramping mode. All measurements were recorded in physiological buffer conditions.

To characterize TiN—NH-chip and captured glioma cells-derived exosomes on TIN-NH-sensing chip, the tapping mode of high-resolution AFM scanner was employed to perform the topography studies on the bare TiN—NH-sensing chip. The functionalized TIN-NH-chip was flushed with deionized (DI) water and dried in nitrogen before conducting the AFM scanning. Similarly, the scanning of captured exosomes on TIN-NH-chip were performed.

11. Exosome Uptake Assay

In the above examples/experiments, ECs (approximately 30,000 cells per well) were cultured on the chamber slide (Lab-Tek™, Thermo Scientific, USA) for 24 hours with normal growth medium supplemented with- and without-lactate at 37° C. in a humidified atmosphere of 5% CO2. On the next day, the cells were washed twice with PBS and replenished again with normal growth medium supplemented with- and without-lactate treated U87 glioma cells-derived exosomes (250 µg), labeled with Exo-Green fluorescent dye (100 µl) (System Biosciences), and further maintained for 24 hours. Next, bEnd.3 cells were washed three times with PBS and fixed with 4% PFA. The actin cytoskeleton of bEnd.3 cells were stained with rhodamine phalloidin conjugated primary antibodies (1:200 dilution) at RT for 1 hour, followed by washing with PBS. Then, it was mounted in Vectashield mounting medium containing DAPI and observed under a laser scanning confocal microscope at 40× magnification.

12. Tube Formation Assay

In the above examples/experiments, 24 hours before the assay, ECs of 80%-90% confluency was treated either with medium with 0.2% FBS. Wells on a 24-well plate were coated with at least 125 µl Geltrex™ (Gibco #A1413201), so the matrix layer would not be too thin which only allow formation of a monolayer of cells. ECs (7×104 cells/well) in 250 µl medium (with the treatment groups as per experimental design) were seeded in each well. After 24 hours, tube formation in ECs was examined under Nikon TS-100-F LED inverted fluorescence microscope and photographed at 40× magnification.

13. Statistical Analysis

In the above analyses, the results were represented as mean±SEM of 3 replicates. Statistical calculation was carried out by either student-t test or one way-ANOVA followed by Dunnett's test for multiple comparison. ** $P<0.01$, * $P<0.05$ were considered significant.

CONCLUSION

The above embodiments have provided sensors and related SPR-based and AFM-based techniques that can be used to reliably detect exosomes closely related with enhanced migration and angiogenesis of glioma, for determining progression of glioma and potentially determining therapeutic efficacy of anti-glioma agents. The sensors and methods can be used independently or can be used to complement existing techniques or tools. The sensors can be used for liquid biopsy in a label-free, non-invasive, and sensitive, and effective manner, and is suited for cancer related applications in particular glioma. The sensors (chips and/or cantilever tip) can be made relatively simply and can be used readily for liquid biopsy.

It will be appreciated by persons skilled in the art that numerous variations and/or modifications may be made to the invention as shown in the specific embodiments without departing from the scope of the invention as broadly described. The described embodiments of the invention should therefore be considered in all respects as illustrative, not restrictive.

For example, the method/sensor/system in the above embodiments may be applied to other types of malignant cancer cells, not necessarily glioma cells, provided that correspondingly suitable biotinylated proteins (e.g., antibodies) are chosen and used. The biotinylated proteins (e.g., antibodies) formed on the surface of the substrate are not limited to biotinylated anti-CD63 antibodies, biotinylated anti-CD44 antibodies, biotinylated anti-EGFRvIII antibodies, etc., but can be any other biotinylated proteins being arranged to engage with surface proteins on exosomes associated with other type of malignant cancer cells. The surface or substrate can be made with made of plasmonic material other than titanium nitride or titanium nitride-based material.

The invention claimed is:

1. A sensor for liquid biopsy, comprising:
a substrate with a surface functionalized with a plurality of first biotinylated antibodies, the surface comprising nano-holes, the first biotinylated antibodies being arranged to engage with first surface proteins on exosomes associated with malignant cancer cells with a first adhesion force capable of capturing the exosomes, wherein the nano-holes are arranged within the surface in a non-periodic manner; and
a cantilever for atomic force microscopy, the cantilever being arranged to be operably cooperating with the substrate, the cantilever including a tip with a tip surface functionalized with a plurality of second biotinylated antibodies being arranged to engage with second surface proteins on the exosomes with a second adhesion force capable of sensing and quantifying the second surface proteins, wherein the second surface proteins are different than the first surface proteins.

2. The sensor of claim 1, wherein the exosomes are released by the malignant cancer cells.

3. The sensor of claim 2, wherein the malignant cancer cells are glioma cells.

4. The sensor of claim 1, wherein the first biotinylated antibodies on the surface of the substrate include biotinylated anti-CD63 antibodies.

5. The sensor of claim 1, wherein the first biotinylated antibodies on the surface of the substrate include biotinylated anti-CD44 antibodies.

6. The sensor of claim 1, wherein the first biotinylated antibodies on the surface of the substrate include biotinylated anti-EGFRvIII antibodies.

7. The sensor of claim 1, wherein the first biotinylated antibodies on the surface of the substrate include one or more of: biotinylated anti-CD63 antibodies, biotinylated anti-CD44 antibodies, and biotinylated anti-EGFRvIII antibodies.

8. The sensor of claim 1, wherein the substrate and the surface are made of the same material.

9. The sensor of claim 1, wherein the substrate and the surface are made of different materials.

10. The sensor of claim 1, wherein the surface is made of plasmonic material.

11. The sensor of claim 10, wherein the plasmonic material comprises titanium nitride or titanium nitride-based material.

12. The sensor of claim 1, wherein the substrate is in the form of a nanofilm of titanium nitride or titanium nitride-based material.

13. The sensor of claim 1, wherein the surface is in the form of a nanofilm of titanium nitride or titanium nitride-based material.

14. The sensor of claim 1, wherein the substrate is in the form of a chip or a disc.

15. The sensor of claim 1, further comprising:
a housing defining a space, the substrate being arranged in the space;
an inlet; and
an outlet;
wherein the inlet, the outlet, and the space are in liquid communication with each other.

16. The sensor of claim 1, wherein the second biotinylated antibodies on the tip surface include biotinylated anti-CD44 antibodies.

17. A method of non-invasive liquid biopsy, the method comprising
providing a solution containing exosomes associated with malignant cancer cells to a sensor comprising
a substrate with a surface functionalized with a plurality of first biotinylated antibodies, the surface comprising nano-holes, the first biotinylated antibodies being arranged to engage with first surface proteins on the exosomes associated with malignant cancer cells with a first adhesion force capable of capturing the exosomes, wherein the nano-holes are arranged within the surface in a non-periodic manner, and
a cantilever for atomic force microscopy, the cantilever being arranged to be operably cooperating with the substrate, the cantilever including a tip with a tip surface functionalized with a plurality of second biotinylated antibodies being arranged to engage with second surface proteins on the exosomes with a second adhesion force capable of sensing and quantifying the second surface proteins, wherein the second surface proteins are different than the first surface proteins; and
detecting exosomes engaged with the surface of the substrate.

18. The method of claim 17, further comprising:
determining a severity of the malignant cancer based on the detection.

19. The method of claim 17, further comprising:
performing localized surface plasmon resonance spectroscopy using the substrate engaged with the exosomes.

20. The method of claim 17, further comprising:
performing atomic force microscopy using the substrate engaged with the exosomes.

21. The method of claim 17, wherein the exosomes are released by the malignant cancer cells.

22. The method of claim 21, wherein the malignant cancer cells are glioma cells.

23. The method of claim 17, wherein the first biotinylated antibodies include one or more of: biotinylated anti-CD63 antibodies, biotinylated anti-CD44 antibodies, and biotinylated anti-EGFRvIII antibodies.

24. A method for making a sensor for liquid biopsy, the method comprising
   providing a substrate with a surface;
   functionalizing the surface with a plurality of first biotinylated antibodies, the surface comprising nano-holes, the first biotinylated antibodies being arranged to engage with first surface proteins on exosomes associated with malignant cancer cells with a first adhesion force capable of capturing the exosomes, wherein the nano-holes are arranged within the surface in a non-periodic manner;
   providing a cantilever for atomic force microscopy, the cantilever being arranged to be operably cooperating with the substrate, the cantilever including a tip with a tip surface; and
   functionalizing the tip surface with a plurality of second biotinylated antibodies being arranged to engage with second surface proteins on the exosomes with a second adhesion force capable of sensing and quantifying the second surface proteins, wherein the second surface proteins are different than the first surface proteins.

25. The method of claim 24, wherein the exosomes are released by the malignant cancer cells.

26. The method of claim 25, wherein the malignant cancer cells are glioma cells.

27. The method of claim 24, wherein the first biotinylated antibodies include one or more of: biotinylated anti-CD63 antibodies, biotinylated anti-CD44 antibodies, and biotinylated anti-EGFRvIII antibodies.

28. The method of claim 24, wherein the surface is made of plasmonic material.

29. The method of claim 28, wherein the plasmonic material comprises titanium nitride or titanium nitride-based material.

30. The method of claim 24, further comprising:
   forming the substrate with the surface.

31. The method of claim 30, wherein the forming the substrate comprises:
   depositing a film made of gold on a glass substrate;
   annealing the glass substrate with deposited gold film such that the gold film at least partly becomes gold nano-islands that are at least partly received in the glass substrate;
   depositing a firm of titanium nitride or titanium nitride-based material on the annealed glass substrate with gold nano-islands; and
   removing the gold nano-islands.

32. The method of claim 31, wherein the annealing is performed for around 9 hours at 500 to 600 degree-Celsius.

33. The method of claim 31, wherein the removing the gold nano-islands is by immersion to a gold-dissolved solution.

* * * * *